(12) United States Patent
Miller

(10) Patent No.: US 11,045,251 B2
(45) Date of Patent: Jun. 29, 2021

(54) GASTRIC TUBE FOR ABLATION PROCEDURES

(71) Applicant: Steven W. Miller, Lake Worth, FL (US)

(72) Inventor: Steven W. Miller, Lake Worth, FL (US)

( * ) Notice: Subject to any disclaimer, the term of this patent is extended or adjusted under 35 U.S.C. 154(b) by 464 days.

(21) Appl. No.: 15/624,526

(22) Filed: Jun. 15, 2017

(65) Prior Publication Data

US 2017/0360503 A1    Dec. 21, 2017

Related U.S. Application Data

(60) Provisional application No. 62/350,274, filed on Jun. 15, 2016.

(51) Int. Cl.
*A61B 18/14* (2006.01)
*A61B 90/00* (2016.01)
(Continued)

(52) U.S. Cl.
CPC ............ *A61B 18/1492* (2013.01); *A61B 5/01* (2013.01); *A61B 17/0218* (2013.01); *A61B 90/04* (2016.02); *A61B 2017/00101* (2013.01); *A61B 2017/00309* (2013.01); *A61B 2017/00314* (2013.01); *A61B 2017/00323* (2013.01); *A61B 2017/00818* (2013.01); *A61B 2018/00029* (2013.01); *A61B 2018/00214* (2013.01); *A61B 2018/00351* (2013.01); *A61B 2018/00494* (2013.01); *A61B 2018/00577* (2013.01); *A61B 2018/00744* (2013.01);
(Continued)

(58) Field of Classification Search
CPC ....... A61B 18/1492; A61B 90/04; A61B 5/01; A61B 17/0218; A61B 2017/00101; A61B 2017/00305; A61B 2017/00314; A61B 2018/00214; A61B 1/32; A61B 2017/0218; A61M 29/00; A61M 29/02
See application file for complete search history.

(56) References Cited

U.S. PATENT DOCUMENTS 6,067,990 A     5/2000  Kieturakis
6,533,772 B1 *  3/2003  Sherts ................ A61M 25/0113
                                                              279/42

(Continued)

*Primary Examiner* — Linda C Dvorak
*Assistant Examiner* — Ryan T Clark
(74) *Attorney, Agent, or Firm* — McHale & Slavin, P.A.

(57) ABSTRACT

An improved gastric tube for displacing a section of an esophagus during cardiac ablation procedures is disclosed. The improved gastric tube is an elongated flexible tube designed to be inserted in the esophagus of a patient and extended past the portion of the esophagus which overlies the heart. The improved gastric tube includes a first lumen extending the length of the tube which receives a control wire, plastic stylet, or other apparatus which would function for displacement of the portion of the esophagus overlying the heart. A second lumen is included which extends to the operative section of the gastric tube, where the esophagus overlies the heart, so that contrast liquid or cooling liquid can be injected into the esophagus at that location. A temperature sensor can also be included to measure the temperature of the esophageal wall, as well as electrodes to connect to a three-dimensional mapping system.

11 Claims, 25 Drawing Sheets

(51) Int. Cl.
  *A61B 5/01* (2006.01)
  *A61B 17/02* (2006.01)
  *A61B 17/00* (2006.01)
  *A61B 18/00* (2006.01)
(52) U.S. Cl.
  CPC ............... *A61B 2018/00797* (2013.01); *A61B 2018/00821* (2013.01); *A61B 2018/1467* (2013.01); *A61B 2218/002* (2013.01)

(56) References Cited

U.S. PATENT DOCUMENTS

| | | | |
|---|---|---|---|
| 7,621,908 B2 | 11/2009 | Miller | |
| 8,529,443 B2 | 9/2013 | Maloney | |
| 2002/0143323 A1 | 10/2002 | Johnston et al. | |
| 2006/0100571 A1 | 5/2006 | Venturelli | |
| 2007/0276324 A1 | 11/2007 | Laduca et al. | |
| 2008/0161890 A1* | 7/2008 | Lafontaine | A61B 18/1492 607/105 |
| 2008/0234693 A1* | 9/2008 | Stefanchik | A61B 17/32056 606/108 |
| 2010/0030098 A1* | 2/2010 | Fojtik | A61B 5/015 600/549 |
| 2010/0317961 A1* | 12/2010 | Jenkins | A61B 5/055 600/411 |
| 2011/0004098 A1* | 1/2011 | Danikas | A61K 49/0017 600/435 |
| 2011/0082488 A1* | 4/2011 | Niazi | A61M 25/1002 606/192 |
| 2013/0006139 A1* | 1/2013 | Tiano | A61B 5/015 600/549 |
| 2013/0060270 A1* | 3/2013 | Teeslink | A61B 17/320783 606/159 |
| 2013/0345628 A1 | 12/2013 | Berger et al. | |
| 2014/0121595 A1* | 5/2014 | Tegg | A61B 1/00133 604/95.04 |
| 2014/0277319 A1* | 9/2014 | Osypka | A61M 25/1002 607/116 |
| 2015/0223866 A1 | 8/2015 | Buelna et al. | |
| 2016/0120614 A1 | 5/2016 | Allmendinger | |
| 2016/0338724 A1* | 11/2016 | Sinelnikov | A61B 17/320068 |
| 2017/0252027 A1* | 9/2017 | Kasic, II | A61B 17/00234 |
| 2018/0317943 A1* | 11/2018 | Razavi | A61B 18/1492 |

\* cited by examiner

GASTRIC TUBE FOR ABLATION PROCEDURES

PRIORITY CLAIM

In accordance with 37 C.F.R. 1.76, a claim of priority is include in an Application Data Sheet filed concurrently herewith. Accordingly, the present invention claims priority to U.S. Provisional Patent Application No. 62/350,274, entitled "GASTRIC TUBE FOR ABLATION PROCEDURES", filed Jun. 15, 2016. The contents of which the above referenced application is incorporated herein by reference.

FIELD OF THE INVENTION

The present invention relates to cardiac ablation procedures and, more particularly, to a gastric tube allowing for displacement of the esophagus during RF (radio frequency) catheter ablation of atrial fibrillation (AF) and other atrial arrhythmias.

BACKGROUND OF THE INVENTION

The goal of surgical treatment for atrial fibrillation is to block or interfere with impulses radiating from ectopic foci inside the pulmonary veins, left or right atrium, and proximal vessels to the heart that trigger atrial fibrillation. One of the first intra-cardiac surgical treatments for atrial fibrillation was demonstrated by the Leipzig group in a procedure, referred to as endocardial linear lesion, to connect the pulmonary vein to the mitral annulus during open heart surgery.

The Mayo Clinic is known for another open heart surgical procedure, termed the Maze procedure, in which multiple cuts are created in the atrial muscle in a maze pattern. These cuts produce scar tissue which blocks electrical impulses through the tissue and, as a result, eliminates the stray impulses causing atrial fibrillation and returns the heart to a normal, coordinated heartbeat.

More recently, cardiology specialists called electrophysiologists have used cardiac catheters to ablate heart tissue without the need for open heart surgery. In this procedure, a radio frequency (RF) catheter is inserted into the atrium and a series of ablations or burns are performed around the mouth of the pulmonary vein and the left atrial wall. The ablations also form scar tissue which blocks stray electrical impulses and restores a normal heartbeat. During RF catheter ablation, lesion depth, extension and volume are related to the design of the ablation electrode and the RF power delivered.

Heart ablations, however, have potential complications, including pulmonary vein stenosis, which can occur if the ablations are too close to the mouth of the pulmonary vein. Another serious complication, which is 80-90% fatal, is atrial-esophageal fistula caused by thermal penetration of the walls of the atrium and esophagus. The atrial-esophageal fistula is most frequently associated with fever, dysphagia, sepsis, stroke, and death.

The atrial-esophageal fistula, or hole in the esophageal wall, may result, in part, from simple anatomy and the RF power needed to develop ablations, as well as the design of the catheter electrode tip and other contributing factors, such as movement of the esophagus during the procedure.

The esophagus is located at the center of the posterior mediastinum, and is separated from the atrium only by the pericardial sac and/or a thin layer of fatty tissue, and is commonly in contact with the atrium. The left atrium wall thickness varies from 1.9-6.5 mm, depending upon the side, and the esophagus thickness is about 2-4 mm. The esophagus is supported at its upper end near the trachea and transits the diaphragm to connect with the stomach. The esophagus is supported at its lower end by the diaphragm. The thoracic portion of the esophagus, between the trachea and the stomach, is mobile and loosely restrained only by soft tissue. This flexibility is necessary to allow the esophagus to move in response to swallowing food, cardiac and lung movement, as well as upper body movements. However, this flexibility of the esophagus complicates the ablation technique and increases the potential for atrial-esophageal fistula.

DESCRIPTION OF THE PRIOR ART

Currently, several techniques are employed by electrophysiologists to reduce the likelihood of an atrial-esophageal fistula developing during the RF atrial ablation. The most comprehensive technique involves a pre-operative procedure of developing a 3-D map of the operative field by CT scan or MRI, which is displayed during the atrial fibrillation ablation procedure with overlapping real time 3-D electro-anatomical maps to reveal the cardiac-esophageal anatomical relationships. This mapping system may, or may not, be used with an esophageal mapping catheter in the esophagus to better locate the position of the esophagus in these three dimensional maps. These mapping systems allow the ablations to be precisely plotted on the atrium wall. The locations of some ablations may be changed or adjusted because of anatomical considerations. Contrast placement within the esophagus lumen may be used independently of CT/MRI to allow real time visualization of the esophagus with fluoroscopy.

In some cases, the electrical energy of the ablation catheter electrode can be controlled, e.g., reducing power in the vicinity of the esophagus. However, the adjustment has not been shown to prevent esophageal injury.

U.S. Pat. No. 7,621,908 discloses an esophageal stylet/catheter for displacing and fixing the position of the esophagus in relation to the atrium of the heart. The disclosed catheter is composed of a long flexible tube to be inserted into the esophagus. A control wire, plastic or metal stylet, or other deflectable apparatus is inserted into the lumen of the catheter tube to change the shape of the catheter and displace the esophagus relative to the heart to reduce the risk of an esophageal fistula resulting from atrial RF ablation.

U.S. Patent Application Publication No. 2016/0120614 discloses a device and method for displacing a lumen within a patient in-vivo during a surgical procedure. More specifically, it relates to displacement control wires used in heart ablation procedures for biasing a patient body portion, e.g., a wall of an esophagus away from or closer to the heart to prevent damage to the esophagus as a result of the heart ablation.

However, the prior art is lacking a way of manipulating the location of the esophagus away from the atrium of the heart during RF ablation which includes a way of introducing a contrast fluid, allowing for assessment of the esophageal lumen diameter.

The prior art also lacks an esophageal manipulation device which includes a temperature probe to detect changes in temperature from an ablation catheter along the trailing edge of the esophagus.

The prior art lacks a method for visualizing the lumen of the esophagus through connecting electrodes placed on the extendable lateral edges of the esophageal catheter with a third party three-dimensional cardiac mapping system such as Biosense Webster Carto3, St. Jude Medical EnSite, and Boston Scientific's Rhythmia mapping systems.

Therefore, what is needed in the art is a device like the esophageal catheter described above, but one that further includes a temperature probe and electrodes which can be connected to a three-dimensional map for real time non-fluoroscopic visualization, as well as a secondary catheter channel allowing for the introduction of radiographic contrast fluid into the area of the esophagus nearest to where the atrial RF ablation is occurring for fluoroscopic confirmation of the trailing edge of the esophagus.

SUMMARY OF THE INVENTION

Therefore, the present invention expands on the prior art and provides a gastric tube for ablation procedures for use with a control apparatus to protect the esophagus of a patient during a surgical procedure. More specifically, the present invention relates to a gastric tube for use with a control apparatus to displace the esophagus of a patient during RF ablation procedures, allows for fluid to be injected through the gastric tube lumen for the purpose of cooling the control apparatus, allows a doctor to measure and control the temperature of the esophageal walls during the procedure, allows electrodes along the sides of the gastric tube to be connected to three-dimensional mapping systems, and allows for the removal of stomach contents and X-Ray contrast material through the gastric tubes of the primary lumen when applied to suction.

Accordingly, it is the primary objective of the present invention to provide an esophageal catheter capable of displacing the esophagus away from certain areas overlying the posterior portion of the heart.

It is a further objective of the present invention to provide a gastric catheter capable of laterally displacing an intermediate portion of the esophagus along the longitudinal axis.

It is yet another objective of the present invention to provide a control wire(s) for insertion through an esophageal catheter to control the longitudinal displacement of the esophagus relative to the heart.

It is a still further objective of the invention to provide an esophageal catheter including temperature probe electrodes to measure the temperature of the esophagus wall during an atrial RF ablation procedure.

It is yet a further objective of the present invention to provide an esophageal catheter allowing for introduction of control fluid at a portion of the esophagus to help regulate esophageal wall temperature and prevent the formation of an esophageal fistula. This control fluid could then be removed through suction applied to the gastric tube at the opening(s) of the distal section of the gastric tube.

It is still yet a further objective of the invention to provide an esophageal catheter which allows contrast fluid to be disposed at the area of the esophagus being displaced to be able to determine esophageal size and ensure that the esophagus has, in fact, been displaced away from the heart of the patient.

It is yet a further objective of the present invention to provide an esophageal catheter allowing for the inclusion of electrodes mounted on an extendable tube along the sides of the gastric tube, which may be connected to three-dimensional mapping systems of other manufacturers. These electrodes may alternate in position with respect to the temperature probe sensors.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

PRIOR ART

PRIOR ART

PRIOR ART

PRIOR ART

PRIOR ART

PRIOR ART

PRIOR ART

PRIOR ART

PRIOR ART

PRIOR ART

PRIOR ART

PRIOR ART

DETAILED DESCRIPTION OF THE INVENTION

Figure 1:
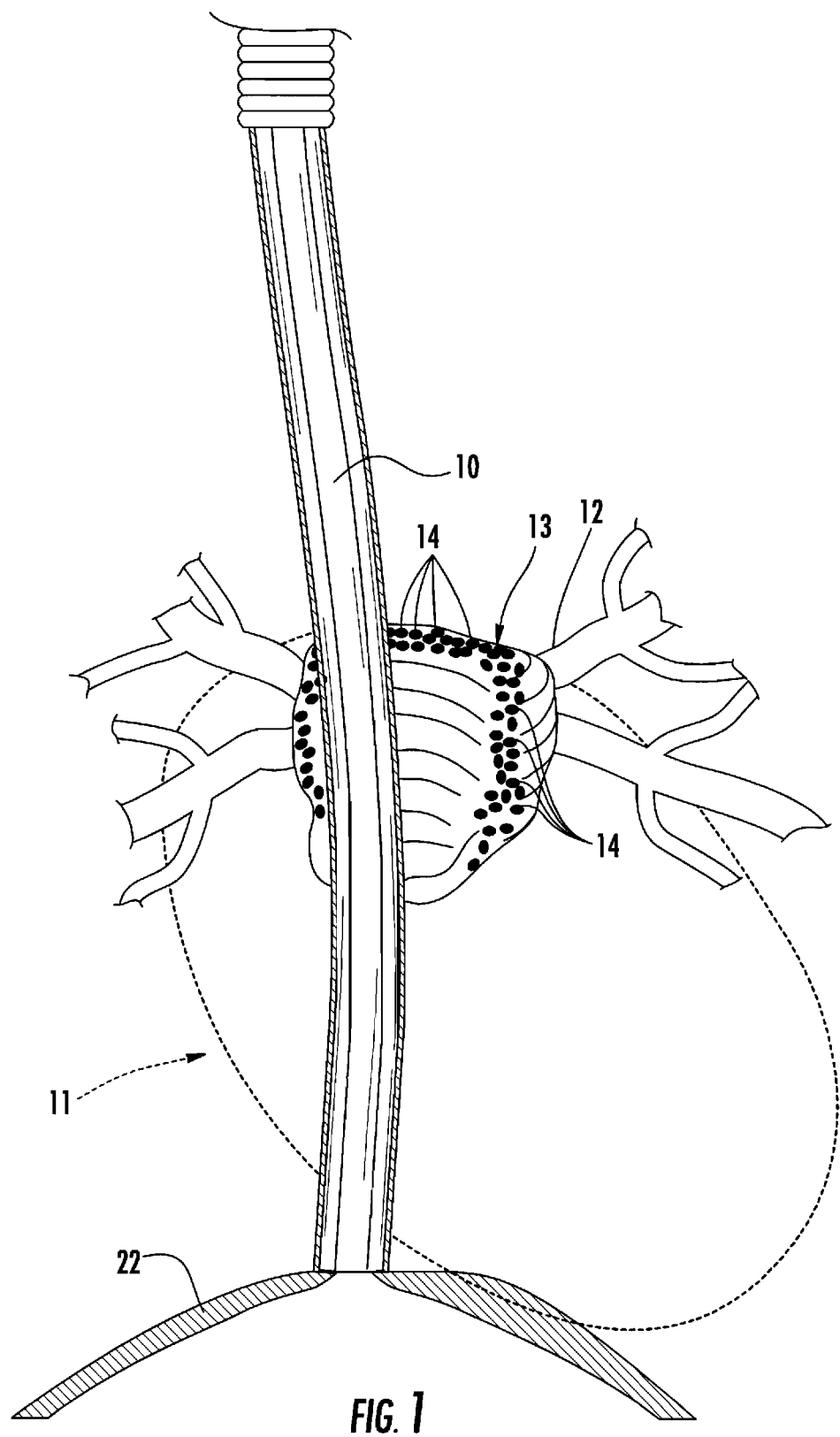
FIG. 1 is a representation of the heart and esophagus, viewed posteriorly, showing a pattern of optimal ablation lesions.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

PRIOR ART FIG. 1, from Miller, illustrates a posterior view of the heart 11 in phantom lines lying in front of the esophagus 10. The esophagus is supported by muscles from the larynx at the superior end and by the diaphragm 22 at the inferior end. Normal anatomical variation in the exact location of the atrium-esophageal relationship does occur. The right pulmonary vein 12 enters the atrium 13, and the desired pattern of optimal ablation lesions 14 are shown as they might appear in the mapping procedure. When viewing these proposed ablation lesions 14, either pre-operatively or intra-operatively, the surgeon may decide to change the location of some of the ablations because of the proximity to the esophagus 10. If a particular ablation(s) is considered necessary, regardless of the location of the esophagus, the RF power to the electrode may be reduced.

Figure 2:
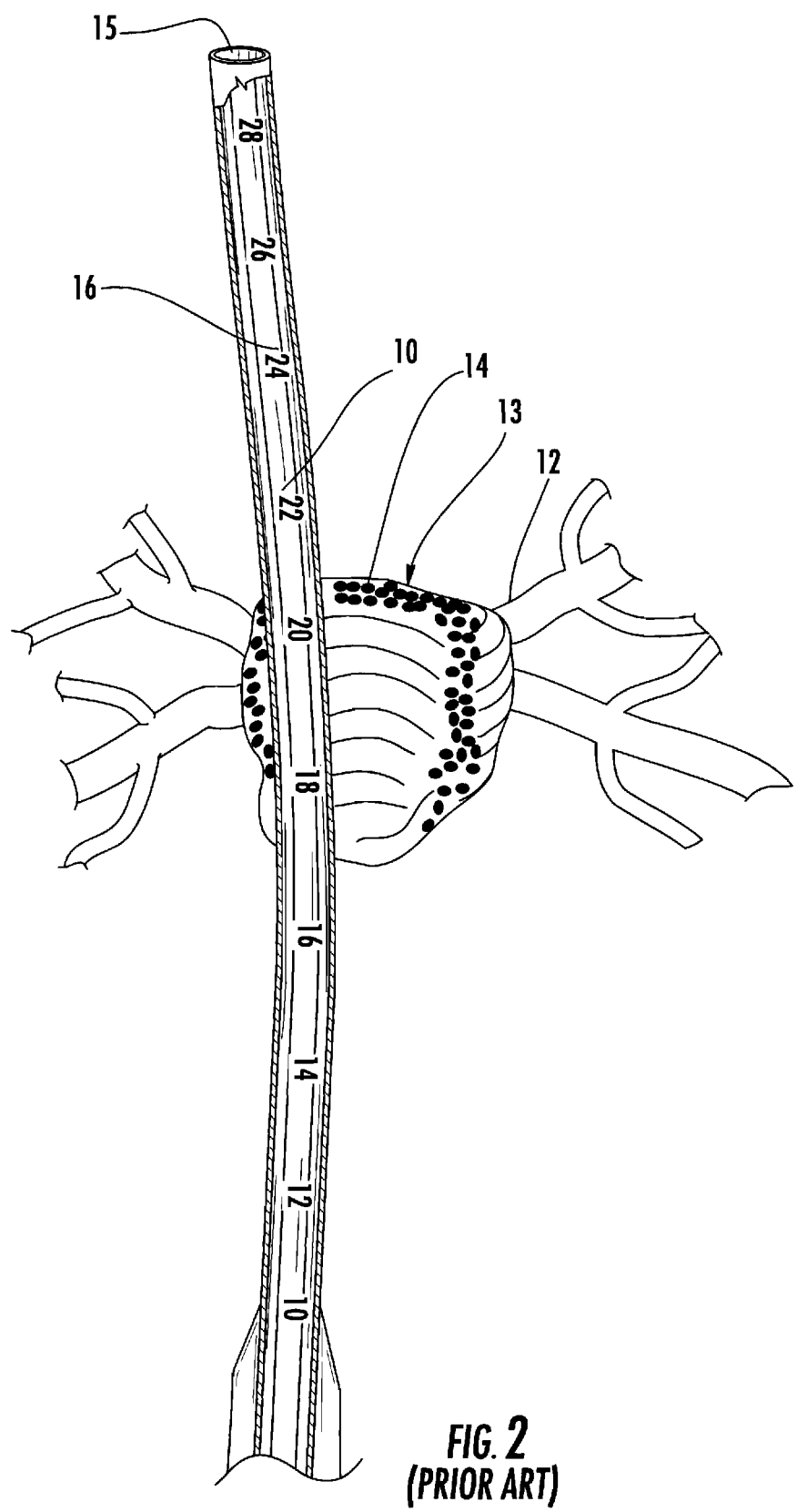
FIG. 2 is a representation of the heart and esophagus of PRIOR ART FIG. 1 with an esophageal catheter inserted.
Figure 3:
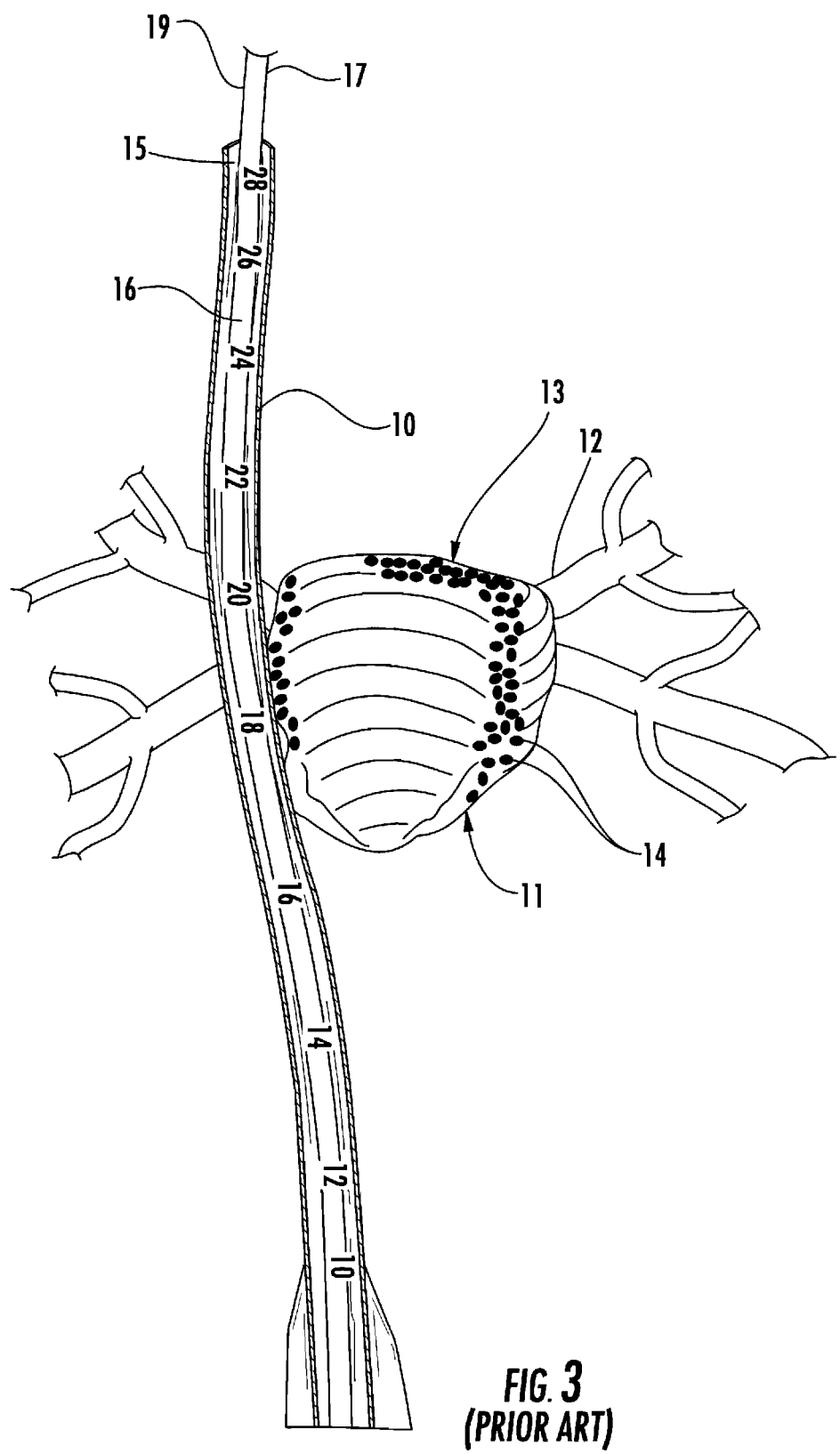
FIG. 3 is a representation of the heart and esophagus of PRIOR ART FIG. 1 with control wires changing the direction of the catheter and esophagus.

To manage the surgical field to eliminate the possibility of an esophageal fistula, an esophageal catheter or gastric tube 15 is inserted through the mouth or nose into the esophagus 10 and through the length of the esophagus past the diaphragm 22, as shown in PRIOR ART FIGS. 2 and 3. The catheter 15 may include a radiologic marker or markers 16 to improve visualization of the location of the catheter 15 and esophagus 10.

Figure 4:
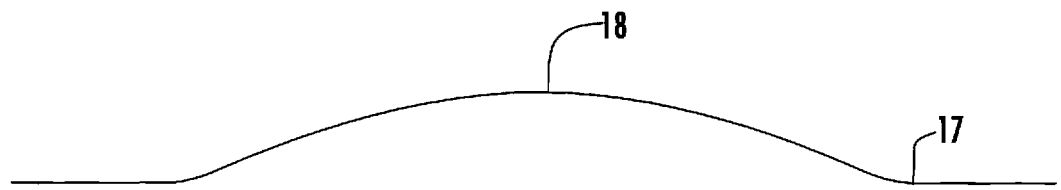
FIG. 4 is a representation of one of the control wires of PRIOR ART FIG. 3.
Figure 5:
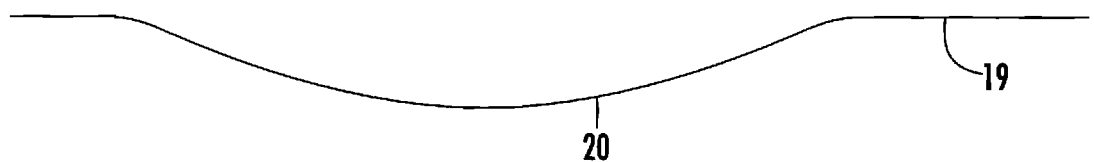
FIG. 5 is a representation of another of the control wires of PRIOR ART FIG. 3.

To move the esophagus laterally, in the surgical field, and to fix the displaced portion of the esophagus beyond the area of thermal lesions, a control wire 17 is inserted through the lumen of the catheter 15. As shown in PRIOR ART FIGS. 4 and 5, the control wires have a preformed curved intermediate portion 18. As the curved portion moves through the catheter, the catheter is displaced along its' longitudinal axis to follow the curve of the control wire. The control wire may be round, flattened, single strand or multi-strand, such as a guide wire. The control wire 17 is manipulated within the catheter to place the curved portion 18 near the atrium and to rotate the control wire to displace the catheter and esophagus away from the ablation lesions 14 laterally and posterior, as the patient's anatomy permits, as shown in PRIOR ART FIG. 3. Depending on the relative size of the catheter lumen 27 and the control wire 17, a second control wire 19 having a similar curved portion 20, as seen in PRIOR ART FIG. 6, may be used. The control wires 17 and 19 may be used in conjunction with each other to produce one curve, or independently to form the catheter in other shapes. The use of separate control wires allows the catheter to remain in place, once inserted, and to be bent in the area dictated by the anatomy of each individual patient. As shown in PRIOR ART FIG. 3, the curvature of the catheter is left lateral, however, the control wires may be manipulated to force the esophagus in the dorsal direction away from the heart or to the right laterally.

Figure 6:
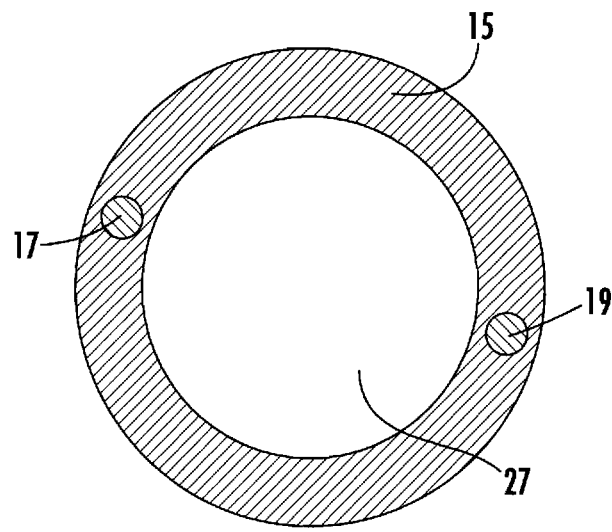
FIG. 6 is a cross section of another esophageal catheter with control wires in the sidewall.
Figure 7:
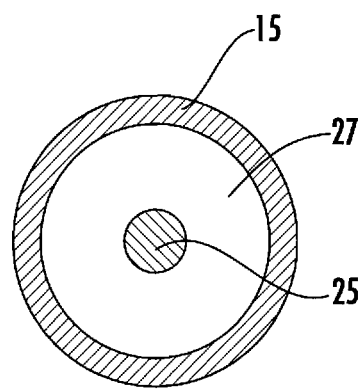
FIG. 7 is a cross section of the esophageal catheter with the control wire in the lumen.
Figure 8:
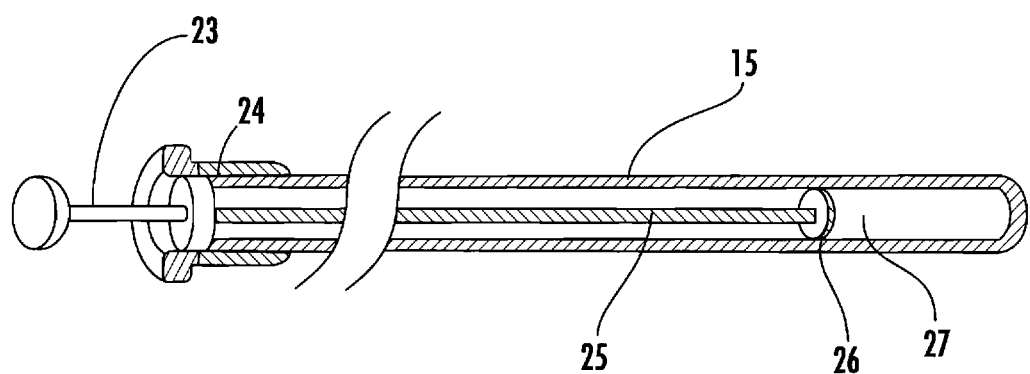
FIG. 8 is a partial longitudinal cross section of another embodiment of the esophageal catheter and control wire.
Figure 9:
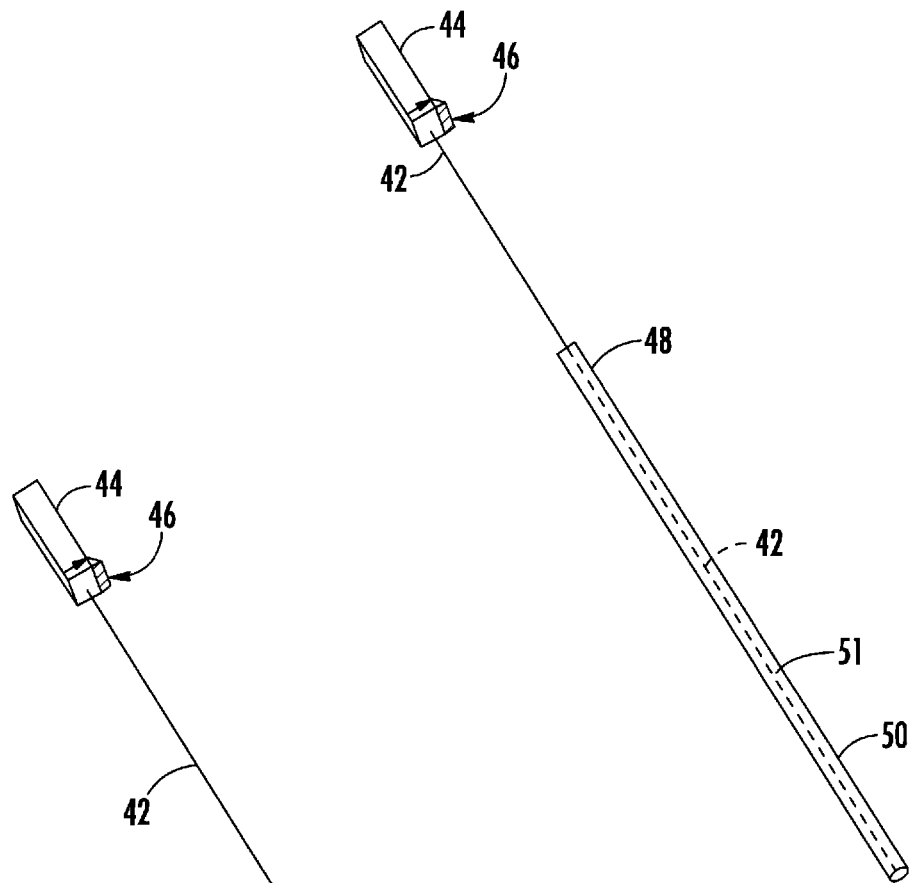
FIG. 9 is a perspective view of an exemplary control wire in a sheathed configuration.

As shown in PRIOR ART FIGS. 6-8, the catheter 15 has control wires attached to the sidewall at discrete points 26 along the catheter. By differential movement of the control wires and the catheter, respectively, the longitudinal shape of the catheter can be changed. Either the plunger 23 or the barrel 24 is moved relative to the other, thereby shortening one member in relation to the other and causing the catheter to bend in the mid-portion. In PRIOR ART FIG. 6, separate control wires 17 and 19 located in the sidewall of the catheter 15 can be moved to bend the catheter in different directions. The control wire 25 is located in the lumen 27 and attached to the side wall at discrete points 26. The catheter may be rotated in the esophagus to move the esophagus as desired.

Referring to PRIOR ART FIGS. 9-12, disclosed is an improved control wire 51 utilizing only a single control wire for biasing a patient body portion, e.g., a wall of the esophagus 41. In the disclosed embodiments, the control wire 51 is constructed from a nitinol material, which in an unused, room temperature or chilled state is straight. When the nitinol wire is inserted into the body, it takes on a curved orientation (preformed) as it is heated to body temperature. In at least one prior art embodiment, the control wire 51 is provided within a tubular sheath 48, which retains the nitinol wire in a straight configuration prior to use, and provides a guideway for the control wire to pass through the mouth or sinus cavity and into the esophagus. In this manner, the sheath 48 prevents the control wire 51 from warming, and thus curving, during insertion while simplifying the traversal of the control wire through the anatomy. Once the sheath reaches the esophagus, the control wire can be extended through the sheath, whereby it is free to interact directly with the esophageal wall 41. When it is no longer necessary to manipulate the esophagus, the control wire can be pulled out through the sheath, and the sheath can be removed or utilized for other needs. Alternatively, the control wire can be retracted into the sheath, and the sheath, along with the control wire, can be removed as a single unit.

In a preferred prior art embodiment, the control wire 51 incorporates a stabilizer member 52 in the form of a spherical ball or the like. The stabilizer member 52 prevents the control wire from perforating or catching the wall of the esophagus during manipulation of the wire to move the esophagus. In addition, the stabilizer member 52 provides an increased surface area on one side of the esophagus so that the curved section of the control wire can force a portion of the esophagus in an opposite direction. This construction prevents perforation of the esophagus and provides a mechanical advantage to the control wire by giving it a surface to push away from with the bend in the control wire.

The prior art control wire in PRIOR ART FIGS. 1-3 and 9-12 utilizes an associated handle 44 with a pointer section 46 to provide a user a frame of reference for displacement, e.g., a pointer may be oriented away from a curve such that displacement will occur away from the pointer's direction. The handle and pointer are preferably attached to the control wire 51 via a process such as injection molding.

In one prior art embodiment, disclosed in PRIOR ART FIGS. 9-12, the control wire comprises a nitinol body 42 and a handle 44 including a pointer section 46. A tubular sheath 48, e.g. PTFE, surrounds the body 42. While the body (or shaft) 42 of the control wire may be any diameter, a diameter of approximately 0.051 inches and length of approximately 36 inches is disclosed as exemplary for esophageal applications. An operative section 50 is illustrated in a straight configuration within the sheath 48 in PRIOR ART FIG. 9.

Figure 10:
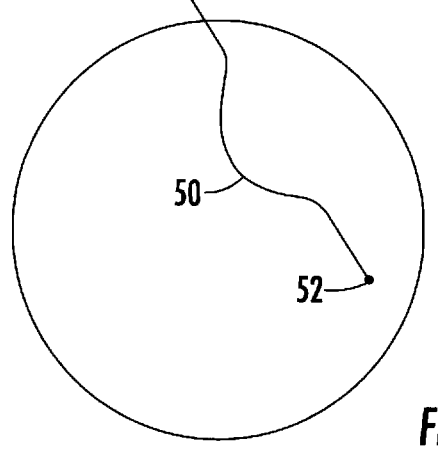
FIG. 10 is a perspective view of the exemplary control wire of PRIOR ART FIG. 9 in an unsheathed configuration.
Figure 11:
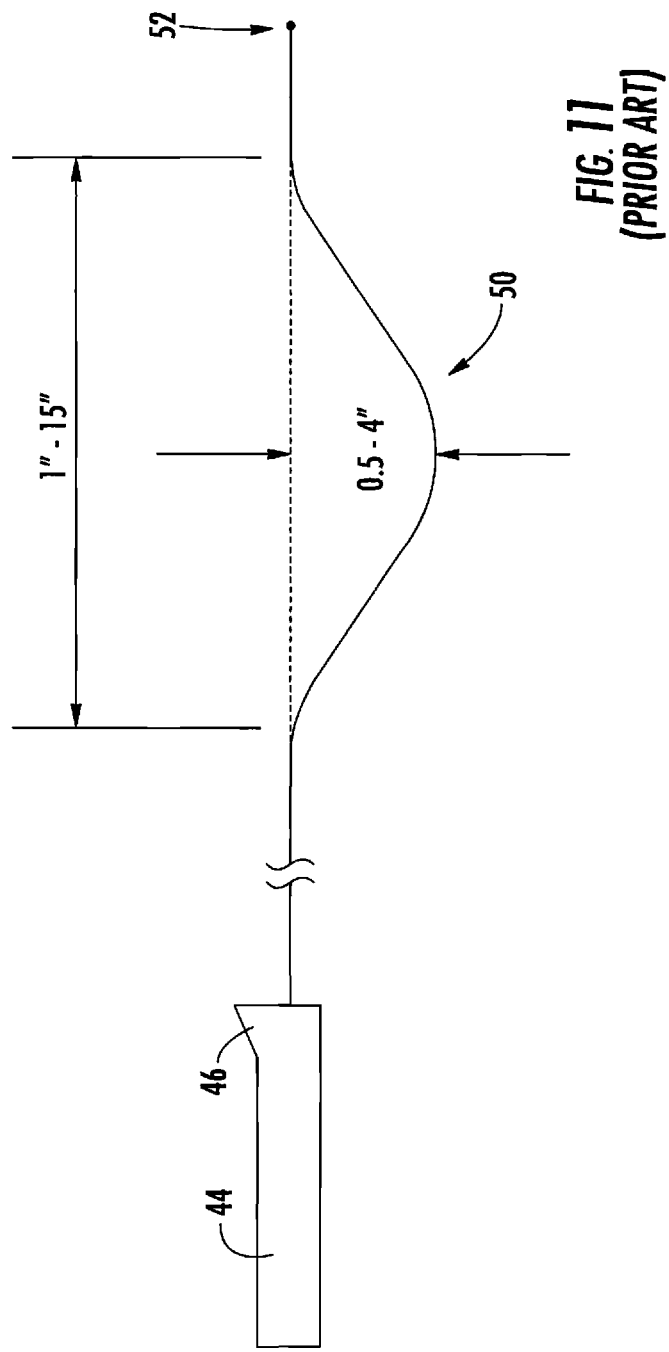
FIG. 11 is a side elevation of an operative section of the exemplary control wire of PRIOR ART FIG. 9.
Figure 12:
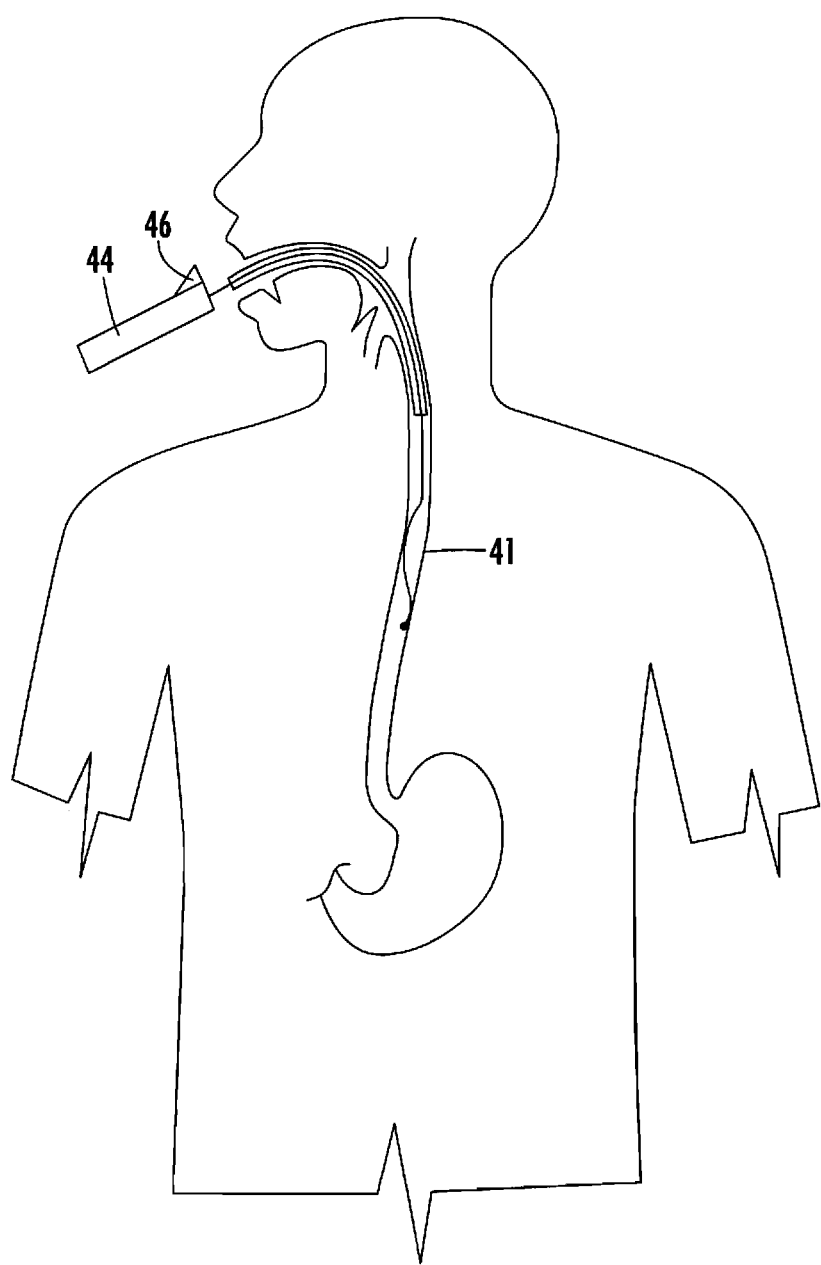
FIG. 12 is a schematic view illustrating the exemplary control wire of PRIOR ART FIG. 9 within the human anatomy.

PRIOR ART FIG. 10-12 illustrates an exemplary prior art control wire in an unsheathed configuration. In this configuration, the operative section 50 takes on a curved configuration due to the warming of the nitinol shaft by body tissues. The stabilizer member 52 facilitates movement of the body 42 within the associated catheter. In this embodiment, the pointer section 46 is provided on a handle 44 opposite the curve of the operative section 50 (thus bias will be away from the side of the pointer). The prior art stabilizer member 52 having an exemplary diameter of approximately 0.110 inches.

Figure 13:
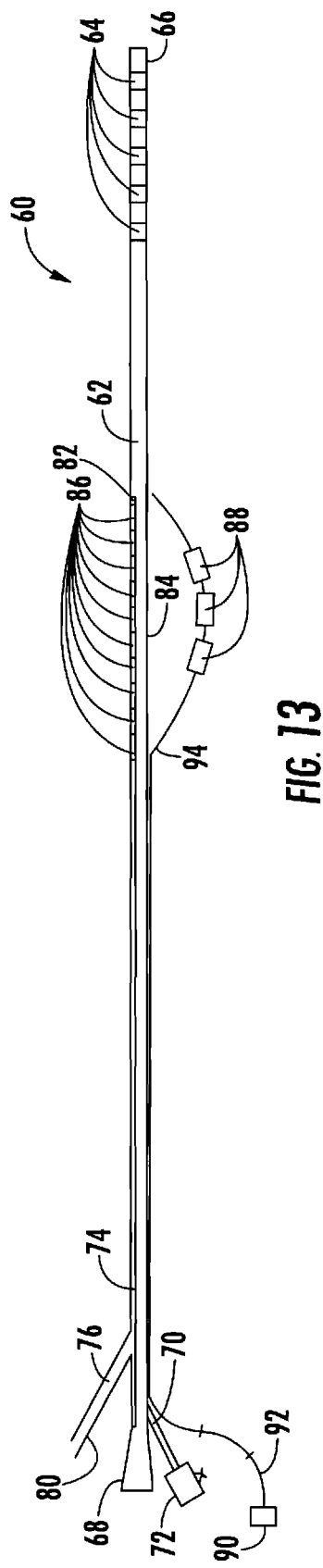
FIG. 13 is a side view of the esophageal catheter of the present invention.
Figure 14:
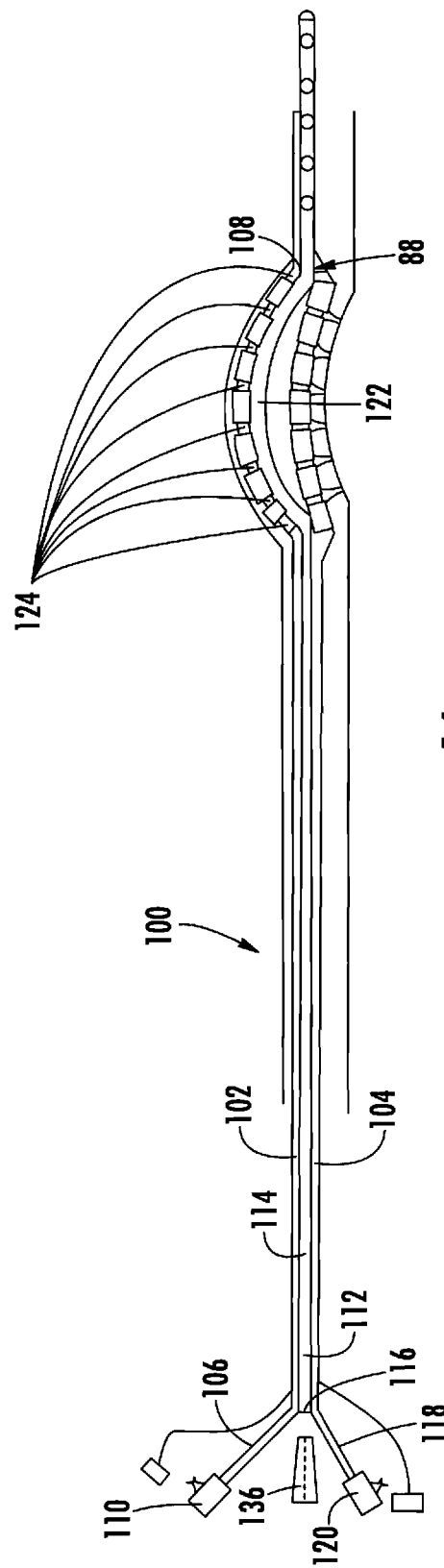
FIG. 14 is a side view of an esophageal catheter of the present invention.
Figure 15:
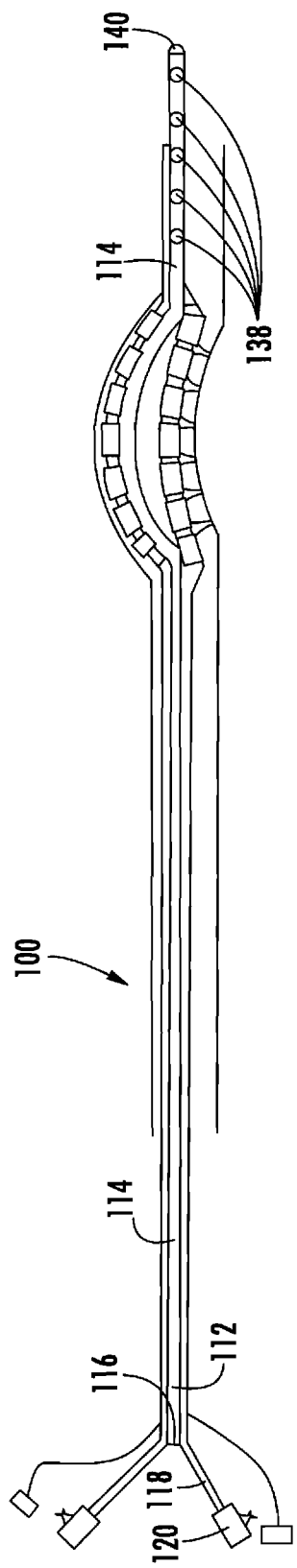
FIG. 15 is a side view of an esophageal catheter of the present invention.
Figure 16:
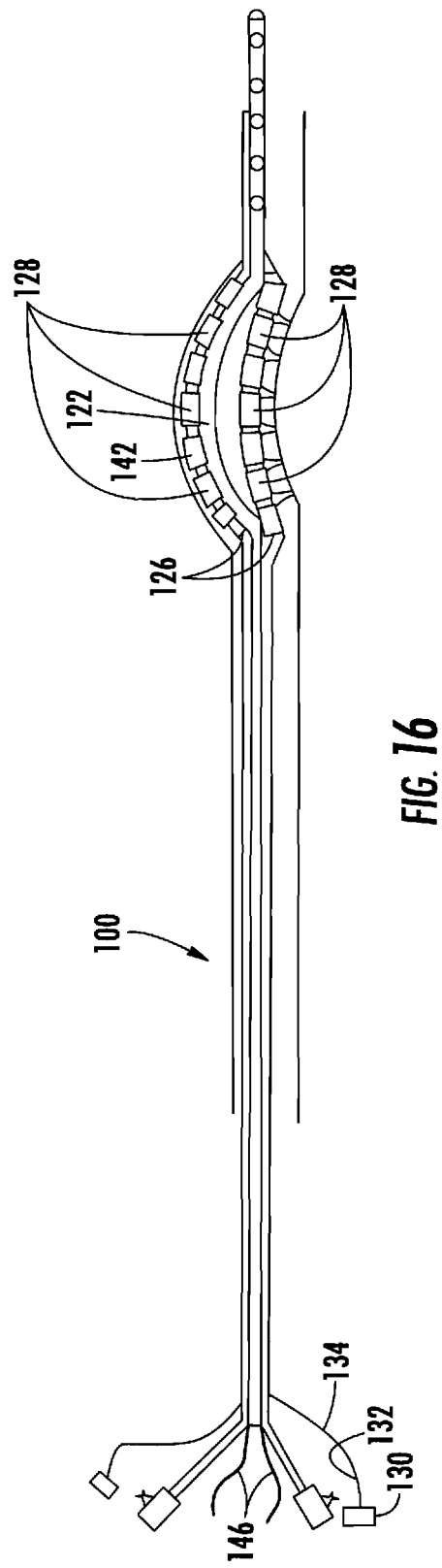
FIG. 16 is a side view of an esophageal catheter of the present invention.
Figure 17:
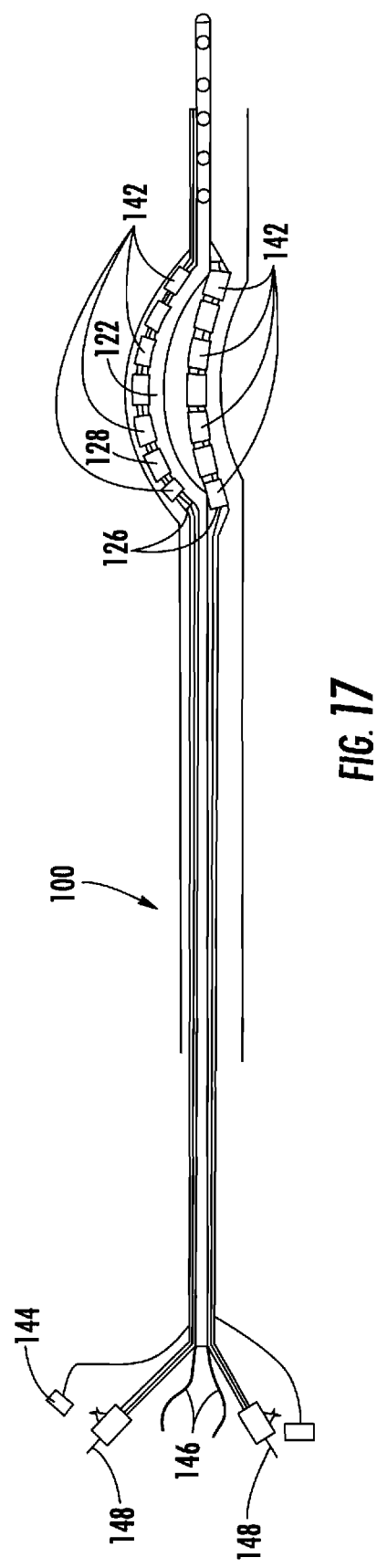
FIG. 17 is a side view of an esophageal catheter of the present invention.
Figure 18:
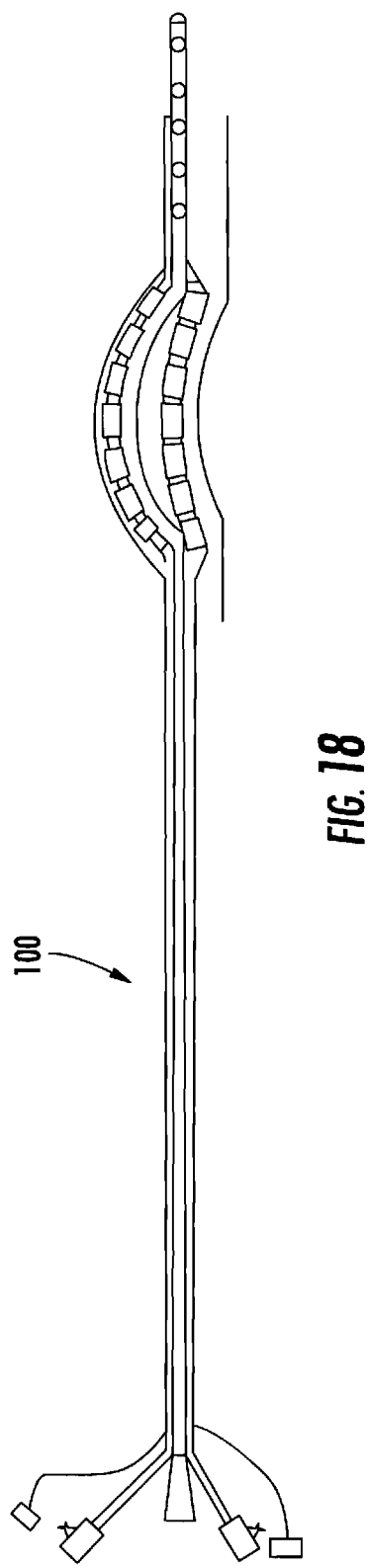
FIG. 18 is a side view of an esophageal catheter of the present invention.
Figure 19:
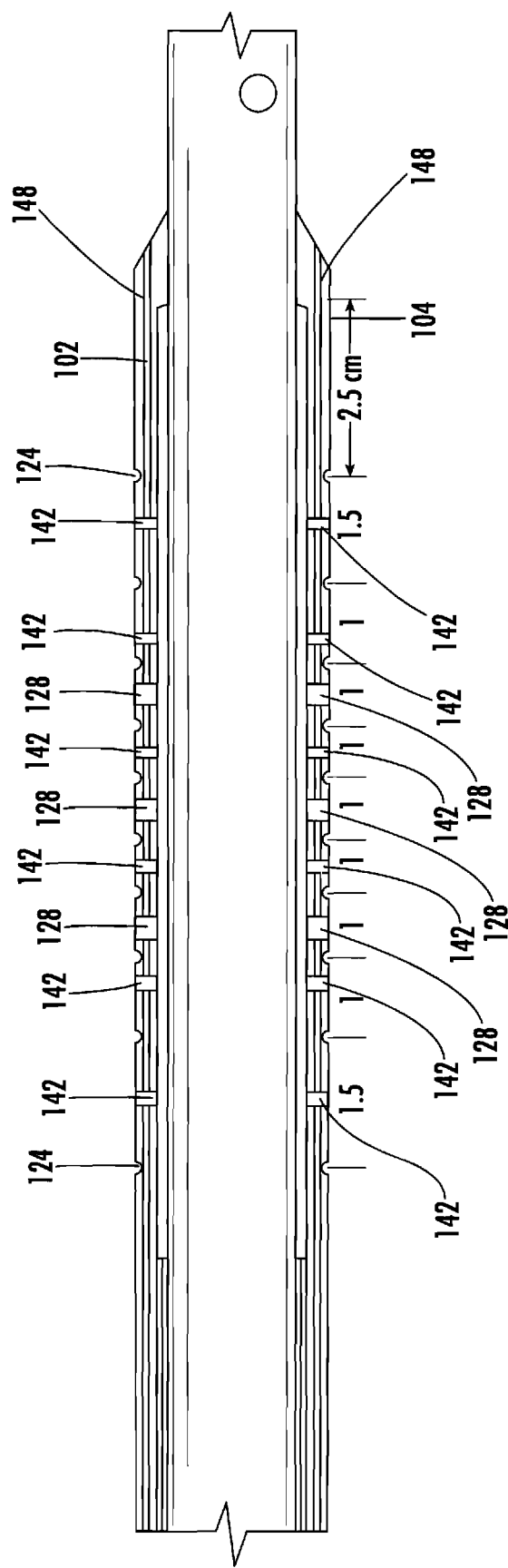
FIG. 19 is a side view of an esophageal catheter of the present invention.

In FIG. 13, an embodiment of the gastric tube 60 of the present invention is disclosed. The gastric tube 60 is similar to a prior art Salem Sump Nasogastric Tube, which is commonly used to remove contents from the stomach of a patient. However, the gastric tube 60 of the present invention is designed to work in cooperation with a control wire (not shown) so as to displace a portion of an esophagus during an ablation procedure.

In the embodiment shown in FIG. 13, the gastric tube 60 has a primary lumen 62 spanning the entire length of the gastric tube 60. The primary lumen 62 can incorporate suction holes 64 at the distal end 66, allowing for suction of liquids out of the stomach of a patient. Including these suction holes 64 allows the gastric tube 60 to additionally function as a conventional Salem Sump Nasogastric Tube. The primary lumen 62 has a proximal end 68 designed to allow a control wire to be inserted for manipulation of a patient's esophagus. Alternatively, the gastric tube 60 can have a pair of opposing control wire lumens (as shown in Prior Art FIG. 6, element 54) to allow for manipulation of the gastric tube 60. The gastric tube 60 can include a stopper 61 to prevent contents from the patient's stomach from filling the primary lumen 62 through the suction holes 64 during manipulation of the esophagus.

A secondary inlet 70 into the primary lumen 62 can be included at the proximal end 68. This secondary inlet 70 should include a valve 72, such as a stopcock, so that it can be opened when desired, and sealed when not in use. Cold water can be injected through the secondary inlet 70 to flush through the primary lumen 62 in order to cool a temperature sensitive control wire and soften the curves for easier removal, or turning of the control wire.

At least one secondary tube with a lumen 74 is provided which extends part way down the gastric tube 60, extending at least far enough to cover the operative section 84 of the gastric tube 60. The secondary tube lumen 74 can include an inlet 76 with a valve 78, such as a two-way stopcock, on the proximal end 80. The secondary tube lumen 74 terminates at a distal end 82 corresponding to an operative section 84 of the gastric tube 60. The operative section 84 is where at least one control wire (not shown) will manipulate the gastric tube 60 to displace the esophagus from the heart during an ablation procedure. The secondary tube lumen 74 includes apertures 86 in the operative section 84 which allow for liquids to be injected into the esophagus.

The apertures 86 on the secondary tube lumen 74 allow contrast liquid to be injected into the esophagus at the operative section 84. The contrast liquid allows a doctor to assess the diameter of the esophagus at the operative section 84 to insure that the trailing side of the esophagus is not still positioned behind the atrium. One method of measuring the esophageal diameter is through fluoroscopy. Measuring the esophageal diameter helps ensure that the esophagus is displaced from the heart wall by the gastric tube 60 and control wire.

The gastric tube 60 can further include a temperature probe 88 extending down to the operative section 84 through the secondary tube lumen 74. The temperature probe 88 includes a standard connector 90 on the proximal end 92 of a wire 94. In one embodiment, the wire 94 of the temperature probe 88 can be made of a nitinol material so that the body temperature can cause the wire to prolapse outward to detect changes in the esophageal wall temperature on the trailing edge of the esophagus. This can allow a doctor to identify if the ablation is causing the esophageal wall to increase in temperature, and if it is likely to cause a fistula.

The apertures 86 on the secondary tube lumen 74 additionally allow for injection of a cooling liquid into the operative section of the esophagus, allowing a user to cool the esophageal wall during an ablation procedure if necessary.

Alternatively, as shown in FIGS. 14-19, the gastric tube 100 can include a pair of secondary tubes with lumens 102, 104 which extend part way down the length of the gastric tube 100. The secondary tubes with lumens 102, 104 include an inlet 106 with a valve 110, such as a two-way stopcock on the proximal end 112, which directs liquid contrast medium towards the secondary tube lumen that is opposite the side of deflection (shown as 104 in the figures). The secondary tubes with lumens 102, 104 terminate at a distal end 108 corresponding to an operative section 122 of the gastric tube 100. The operative section 122 is where the control wire, or wires, and gastric tube 100 will displace the esophagus from the heart during an ablation procedure. The operative section 122 of the secondary tubes with lumens 102, 104 include apertures 124, allowing for liquids to be injected into the esophagus. The main body of the gastric tube 100 can include a pair of opposing control wire lumens to allow a pair of control wires 146 to manipulate the gastric tube 100 in the operative section 122.

The primary lumen 114 has a primary inlet 116 and a secondary inlet 118 on the proximal end 112. The secondary inlet 118 can include a valve 120, such as a stopcock, so that it can be opened when desired, and sealed when not in use. The primary lumen 114 should also include a stopper 136 to prevent contents from a patient's stomach from filling the primary lumen 114 through suction holes 138 at the distal end 140 during manipulation of the esophagus.

The apertures 124 on the secondary tube lumens 102, 104 allow for contrast liquid to be injected into the esophagus at the operative section 122 towards the trailing edge of the esophagus.

The gastric tube 100 can further include a temperature probe 126 extending down to the operative section 122; the temperature probe 126 consisting of one or more temperature sensors, or thermistors, 128 attached to a secondary wire 134, and including a standard connector 130 on the proximal end 132. In one embodiment, the secondary wire 134 can be made of a nitinol material so that the body temperature can cause the wire to prolapse outward to detect changes in the esophageal wall temperature on the trailing edge of the esophagus.

The temperature probe 126 can further include electrodes 142 on the secondary wire 134, alternating with the temperature sensors 128. The electrodes 142 would be connected to an adapter 144, at the proximal end, which connects to a 3-dimensional mapping system, such as the Biosense Webster Carto 3, the St. Jude Medical EnSite, Boston Scientific Rythmia, Medtronic CardioInsight, or other such systems. Many electrophysiologists prefer to function with minimal fluoroscopy and the juxtaposition of the real-time esophagus position, with the left atrium and ablation catheters providing data on the exact location of the esophagus.

The secondary tubes 102, 104 can each include a separation wire 148, whereby tension on the separation wire 148 can pull the trailing secondary tube away from the gastric tube 100, thus allowing a user to place the temperature sensors 128 and electrodes 142 along the trailing esophageal wall during use.

Figure 20:
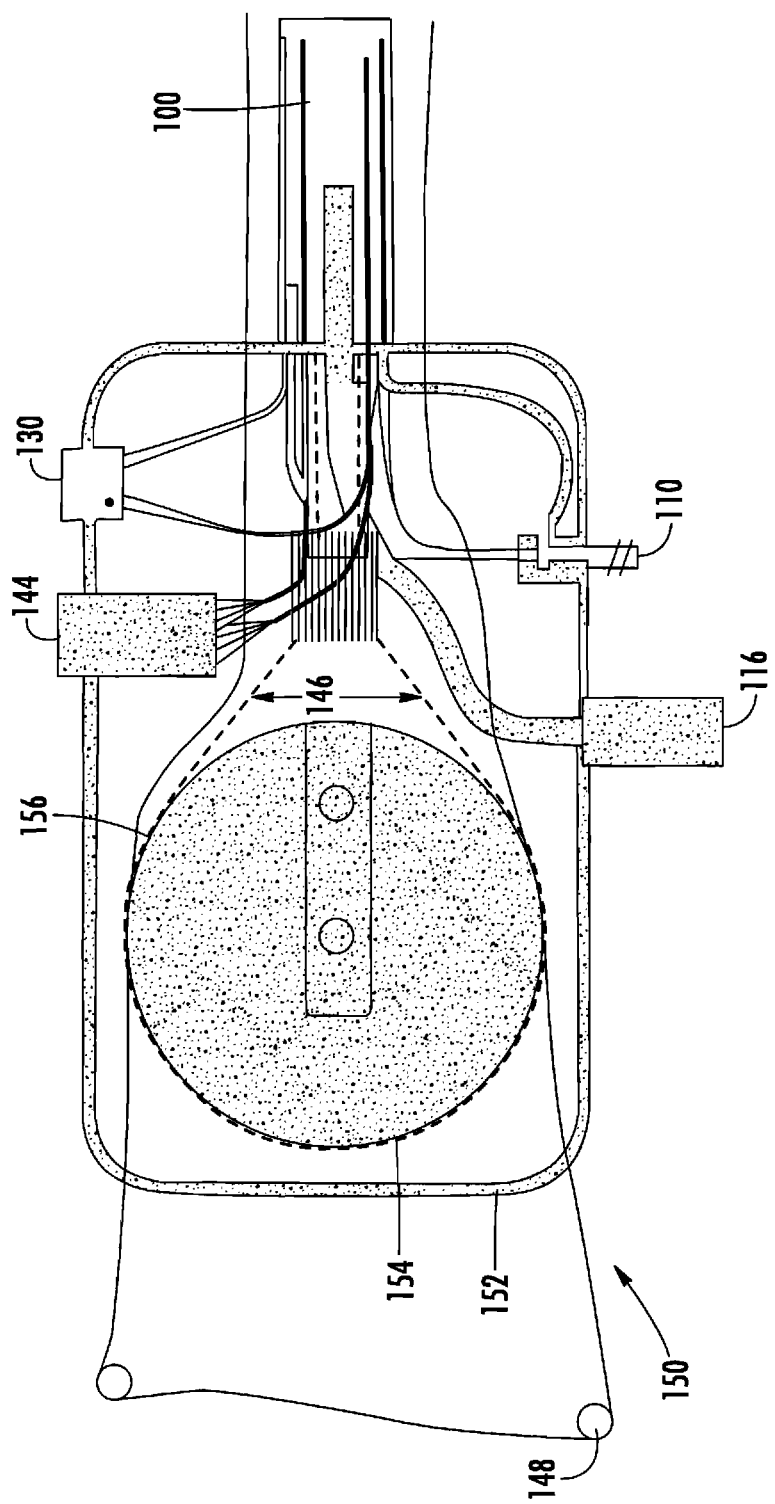
FIG. 20 is a top view of a control box for an esophageal catheter of the present invention.
Figure 21:
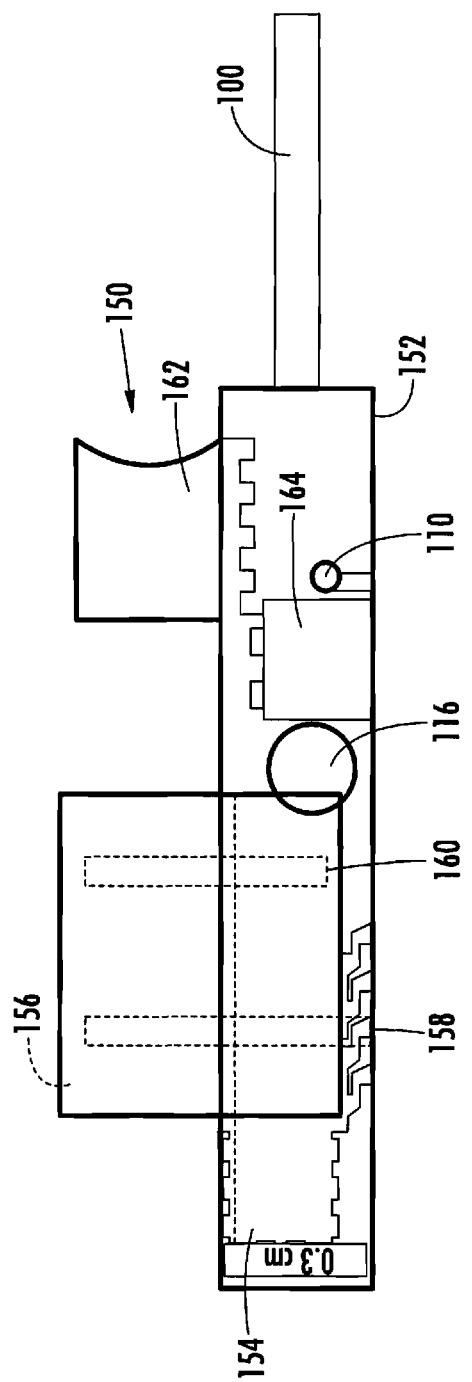
FIG. 21 is a right-side view of the control box of FIG. 20.
Figure 22:
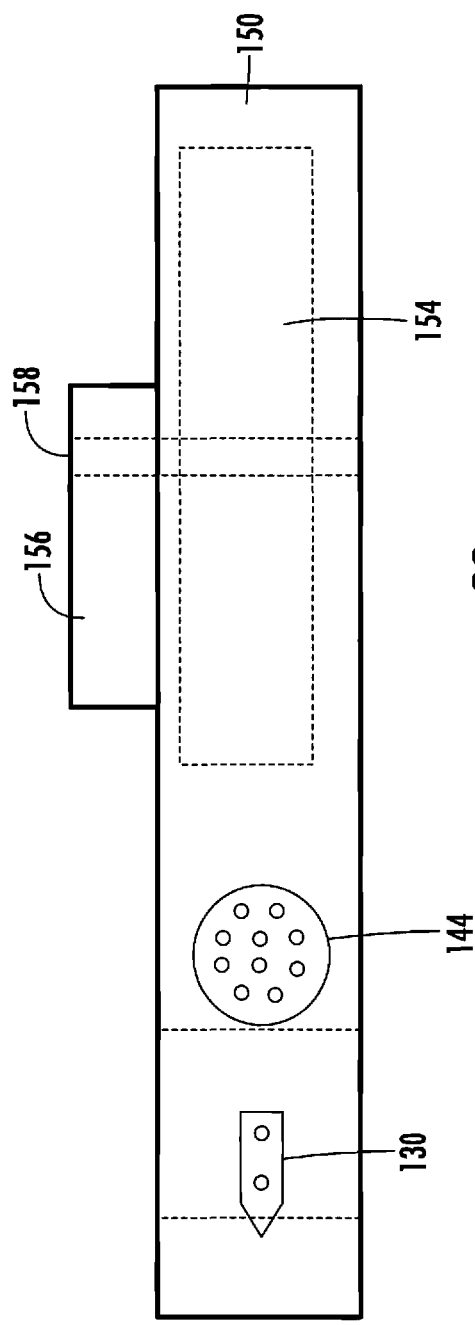
FIG. 22 is a left-side view of the control box of FIG. 20
Figure 23:
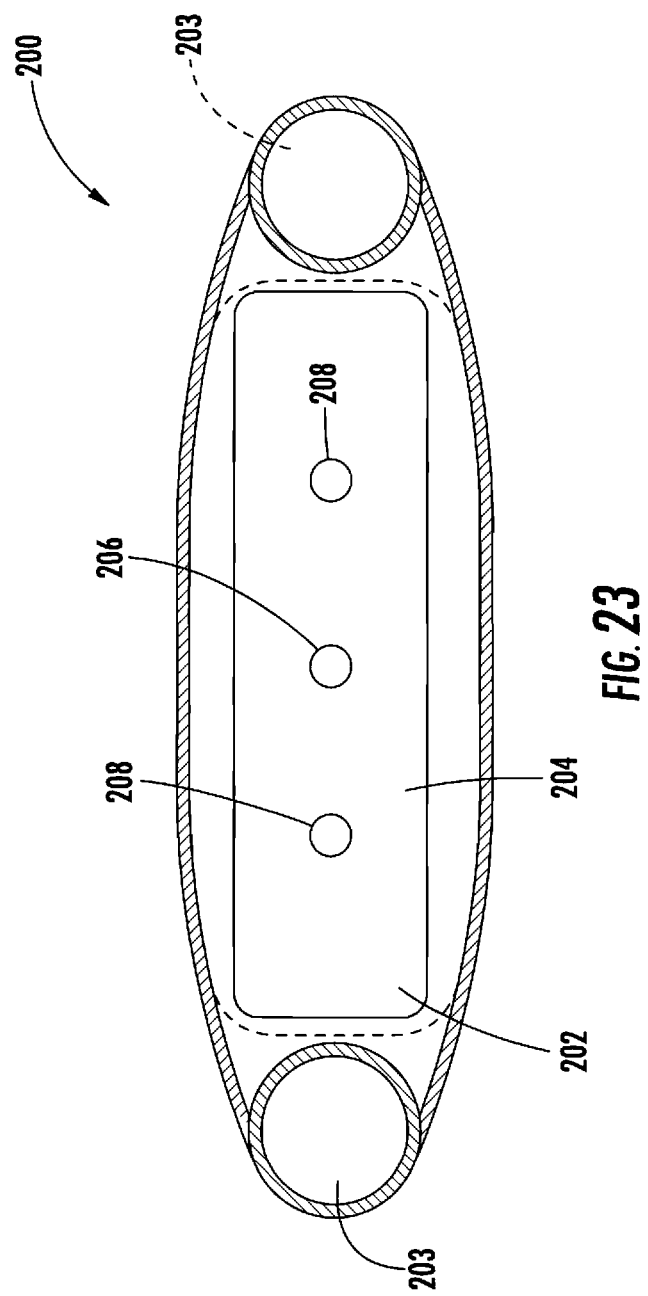
FIG. 23 is a front end view of an embodiment of the present invention utilizing a segmented main body.
Figure 24:
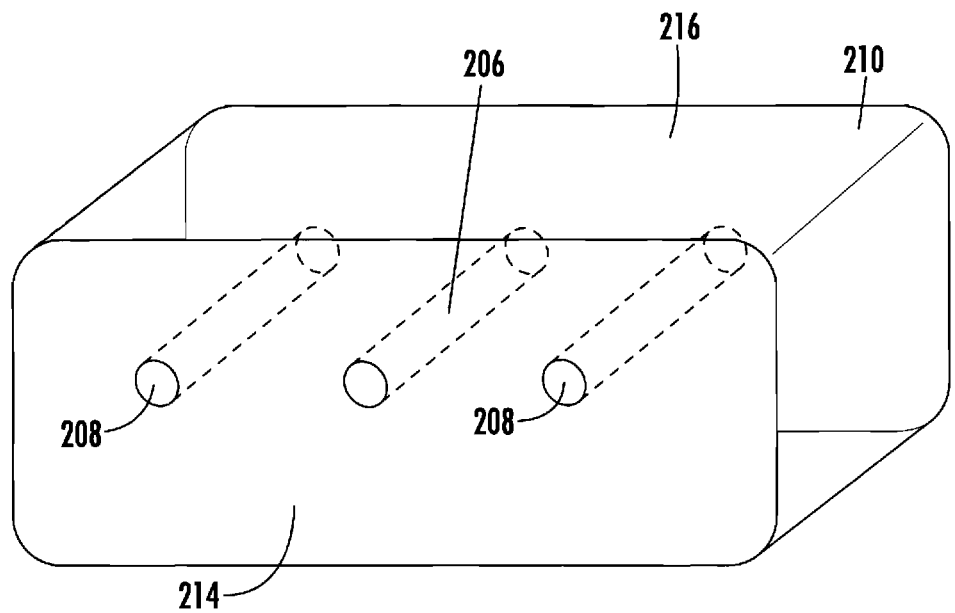
FIG. 24 is a perspective view of a straight-section segment of the embodiment of FIG. 23.
Figure 25:
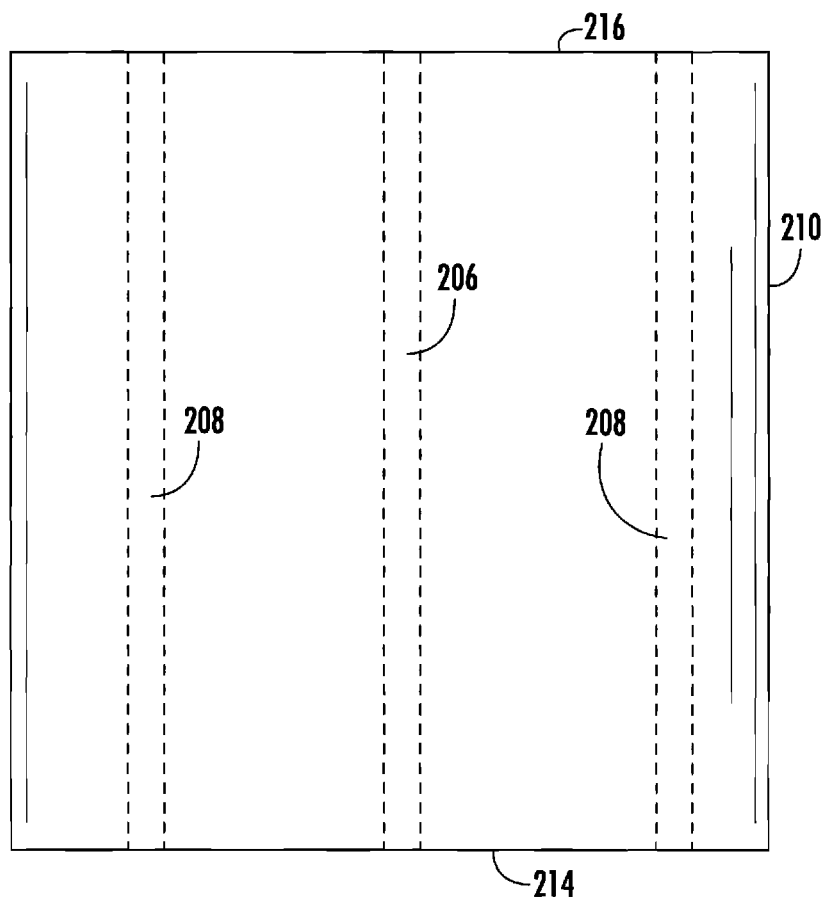
FIG. 25 is a top view of the straight-section segment of FIG. 24.
Figure 26:
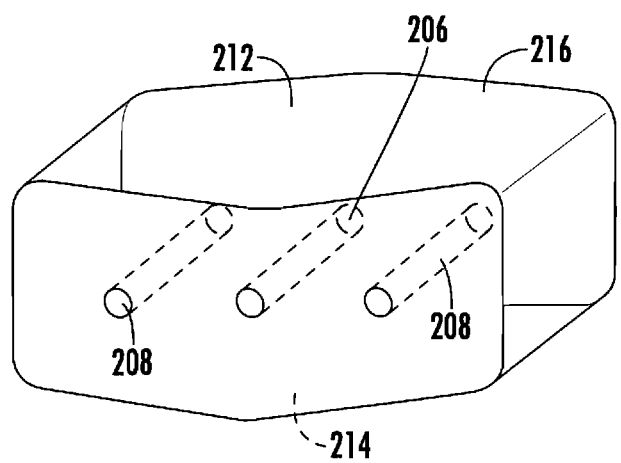
FIG. 26 is a perspective view of an angled-section segment of the embodiment of FIG. 23.
Figure 27:
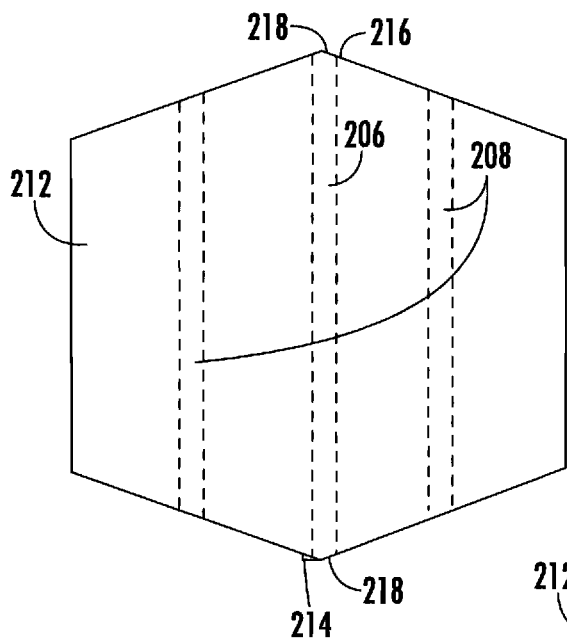
FIG. 27 is a top view of the angled-section segment of FIG. 26.

FIGS. 20-22 depict a control box 150 for a gastric tube 100. The control box 150 includes a housing 152 for more easily managing the control of the gastric tube 100. The proximal end of the gastric tube 100 connects to the control box housing 152. The valve 110, shown as a three-way stopcock, that feeds into the secondary tubes 102, 104 is coupled to the housing 152, with all connections maintained within the housing. Similarly, the thermocouple connector 130 is coupled to both the housing 152 and to the secondary wires 134 which connect to the temperature sensor thermistors 128. An adapter 144 for connecting to a 3D mapping instrument is also coupled to the housing 152, and connects through wires 135 to the electrodes 142.

The pair of opposing control wires 146 can attach to a tension control. The tension control depicted is a deflection disk 154. The deflection disk 154 allows tension to be applied to one of the pair of control wires 146 while releasing tension to the opposite control wire 146. The deflection disk 154 has a handle 156 which is outside of the housing 152. An axle 158 attaches through the handle 156 and the deflection disk 154 to the housing 152. A second attachment pin 160 secures the handle 156 to the deflection disk 154.

When the desired tension is achieved, a user can pull on the center tension slide pull 162 which frictionally engages with the guide 164 within the housing 152. The guide 164 directs the pair of opposing control wires 146 to opposite sides of the deflection disk 154. When the slide pull 162 is operated by a user, it slides towards to the deflection disk 154 and pinches the control wires 146 against the guide 164, thus maintaining a desired tension in the pair of opposing control wires 146.

Figure 28:
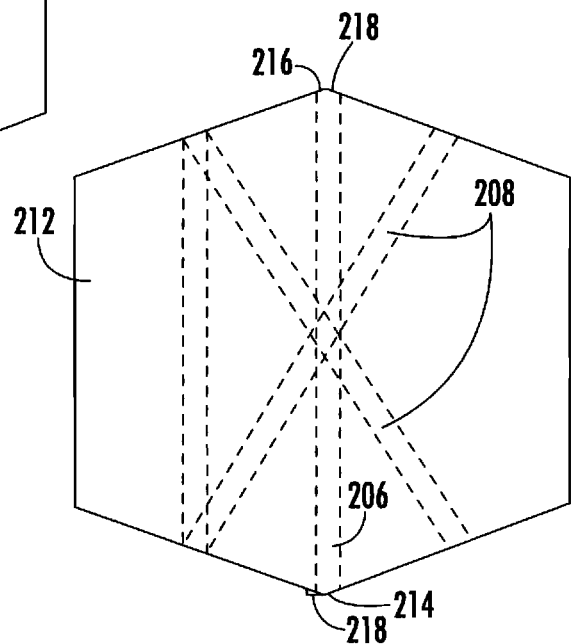
FIG. 28 is a top view of an angled-section segment.

In FIGS. 23-30, an alternate gastric tube 200 is shown. This embodiment still maintains a primary flexible elongated body 202 and a pair of secondary tubes with lumens 203. The difference in this gastric tube 200 is that the primary elongated flexible body 202 is segmented in different body segments 204. Each piece includes a centrally located primary lumen 206, and a pair of control wire lumens 208. The body segments 204 are designed for either straight sections 210, or angled sections 212. Each body segment 204 has a proximal surface 214 and a distal surface 216, where the lumens 206, 208 extend from the proximal surface 214 to the distal surface 216. The straight-section segments 210, shown in FIGS. 24-25 have proximal and distal surfaces 214, 216 that are perpendicular to the primary lumen 206. The angled-section segments 212, shown in FIGS. 26-28, have proximal and distal surfaces 214, 216 that are angled around an apex where the primary lumen 206 extends through the segment 212. By having a central peak 218, the angled-section segments 212 aid in the curvature of the flexible body 202 over the operative section 220. The angled-section segments 212 have two basic forms, one where the primary lumen 206 and control wire lumens 208 are all parallel (FIG. 27), and a second form where the control wire lumens 208 cross within the segment 212 (FIG. 28).

Figure 29:
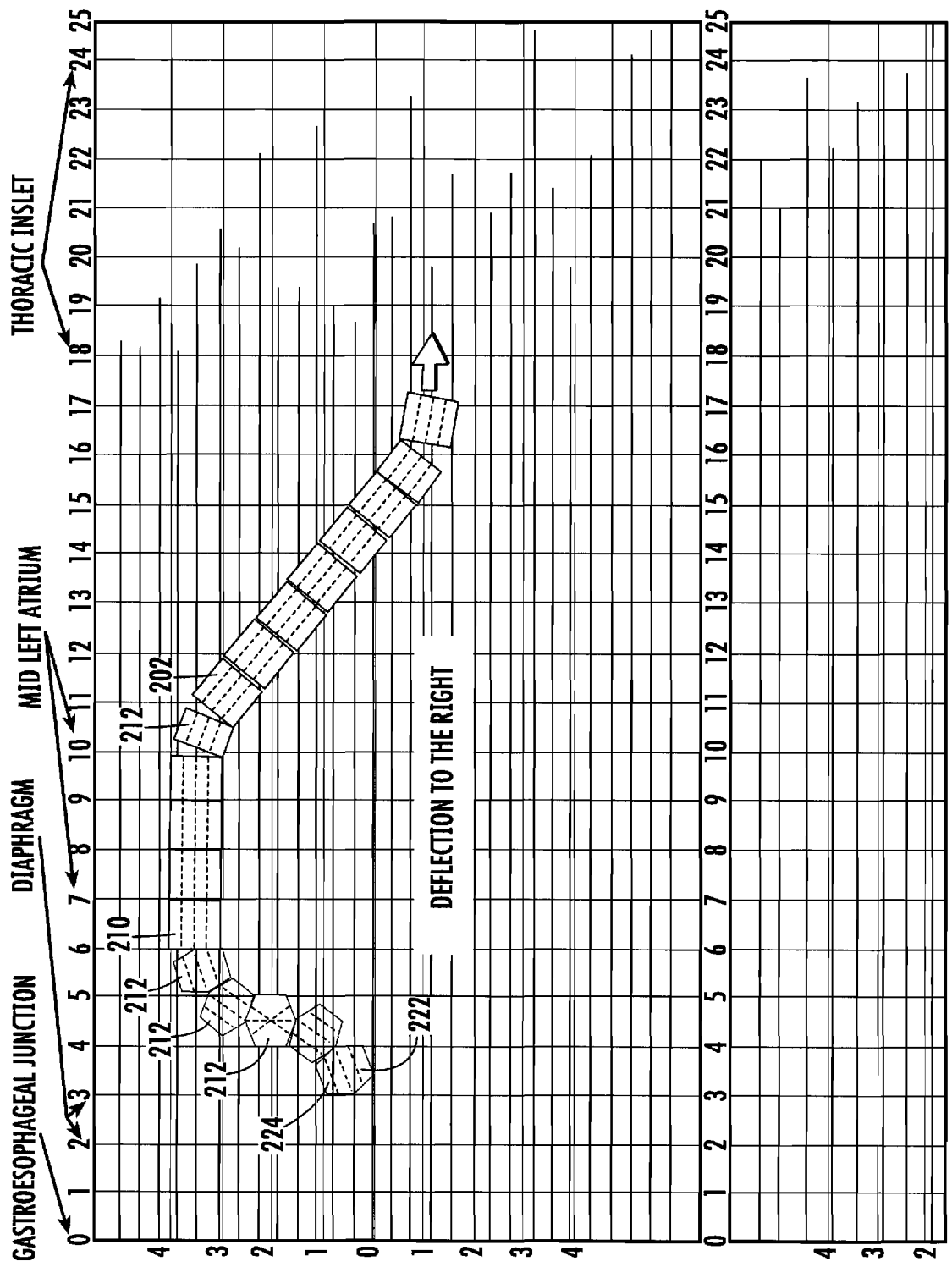
FIG. 29 is a side view of the operative section of the embodiment of FIG. 23.
Figure 30:
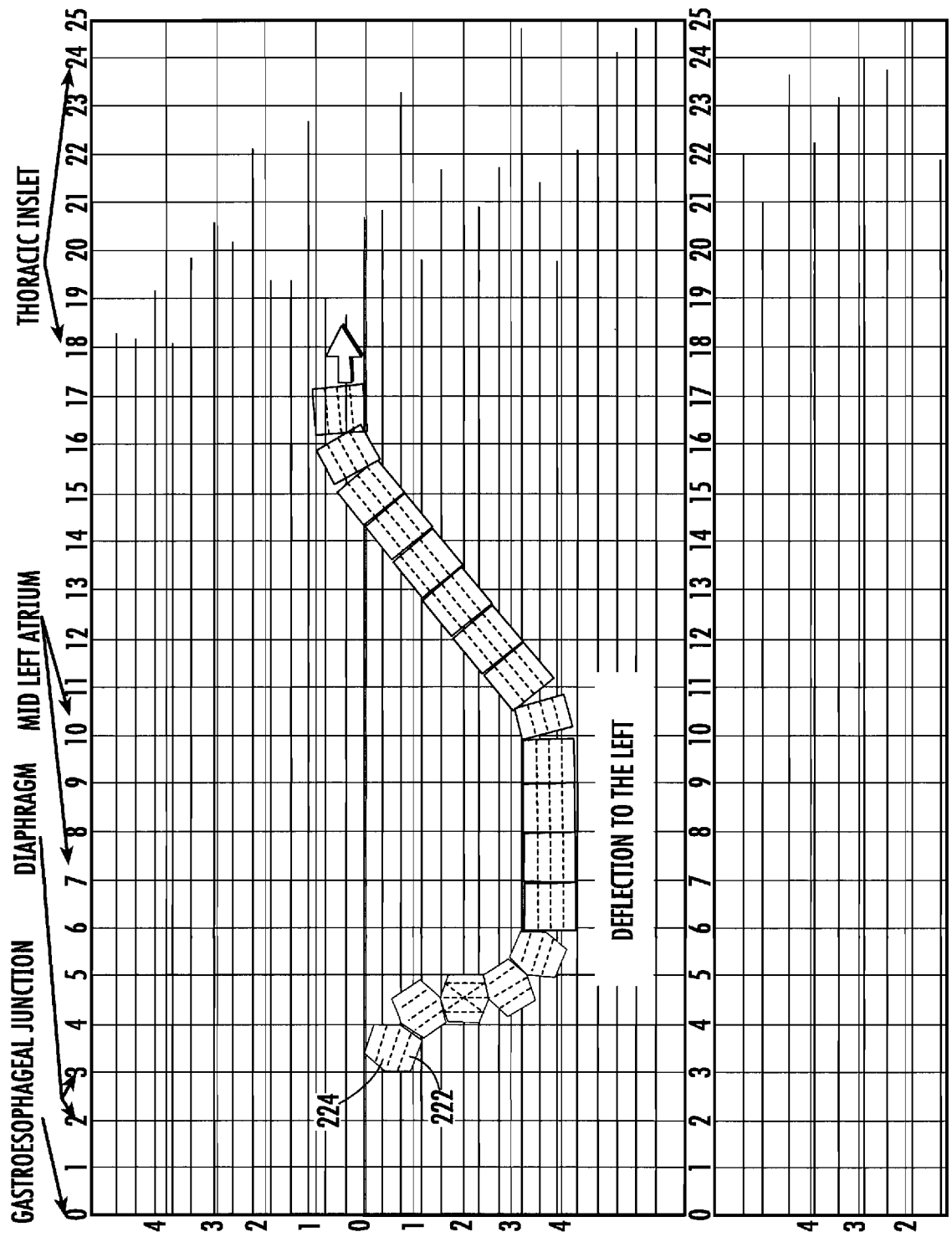
FIG. 30 is an alternate side view of the operative section of the embodiment of FIG. 23.

As shown in FIGS. 28-29, the primary elongated flexible body 202, and therefore the gastric tube 200, can deflect to either side because of the varying body segments 204. Following the path of the right control wire 222 and left control wire 224 though the flexible body 202, it can be seen that, by providing a series of angled-section segments 212, the flexible body can be curved when a control wire is under tension. As shown in FIG. 29, because an angled section segment 212 with crossing control wire lumens is employed, when the left control wire 224 is under tension, and thus shortening its path, the flexible body 202 will curve to the left. Then, by positioning a series of straight-section segments 210 and angled-section segments 212, the flexible body 202 can be constructed to conform to a curved shape and thus displace an esophagus over an operative section 220. Conversely, as shown in FIG. 30, tension in the right control wire 224 results in a deflection of the flexible body 202 to the right over the operative section 220.

Figure 31:
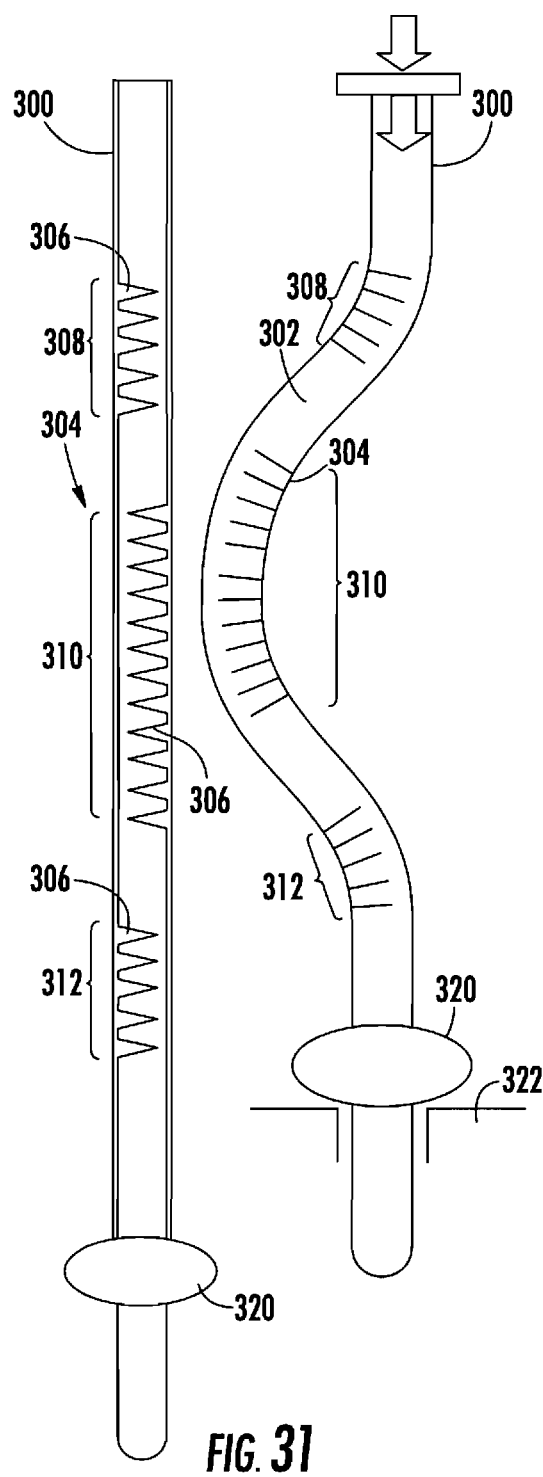
FIG. 31 is a side view of a notched-body embodiment of the present invention illustrated in straight and curved forms.
Figure 32:
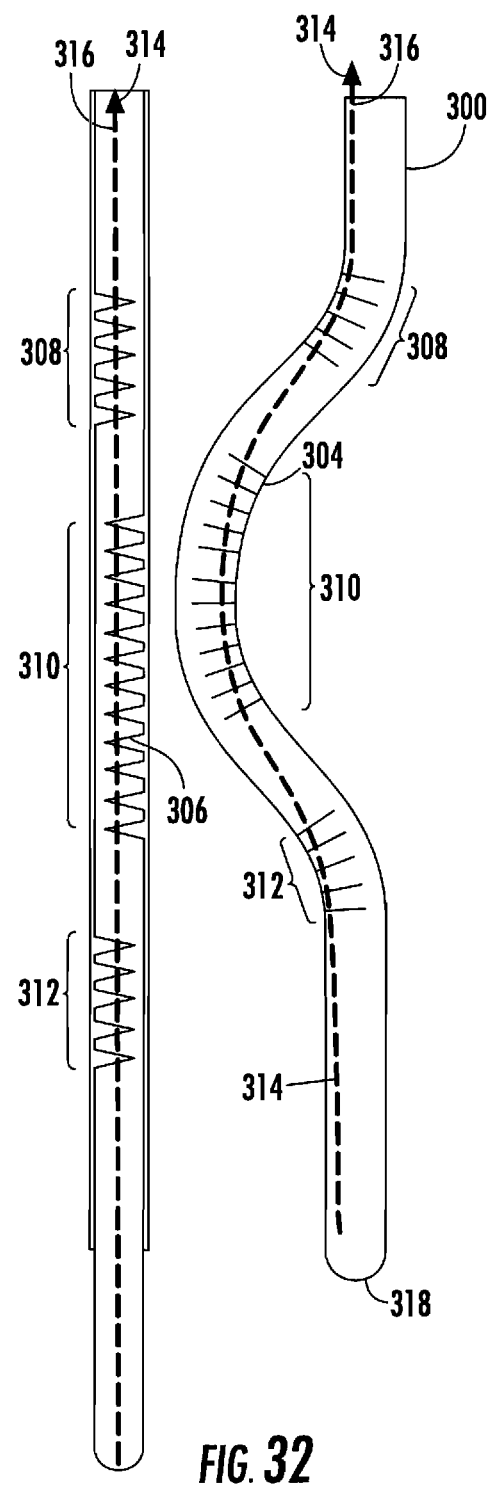
FIG. 32 is a side view of a notched-body embodiment of the present invention in straight and curved forms.
Figure 34:
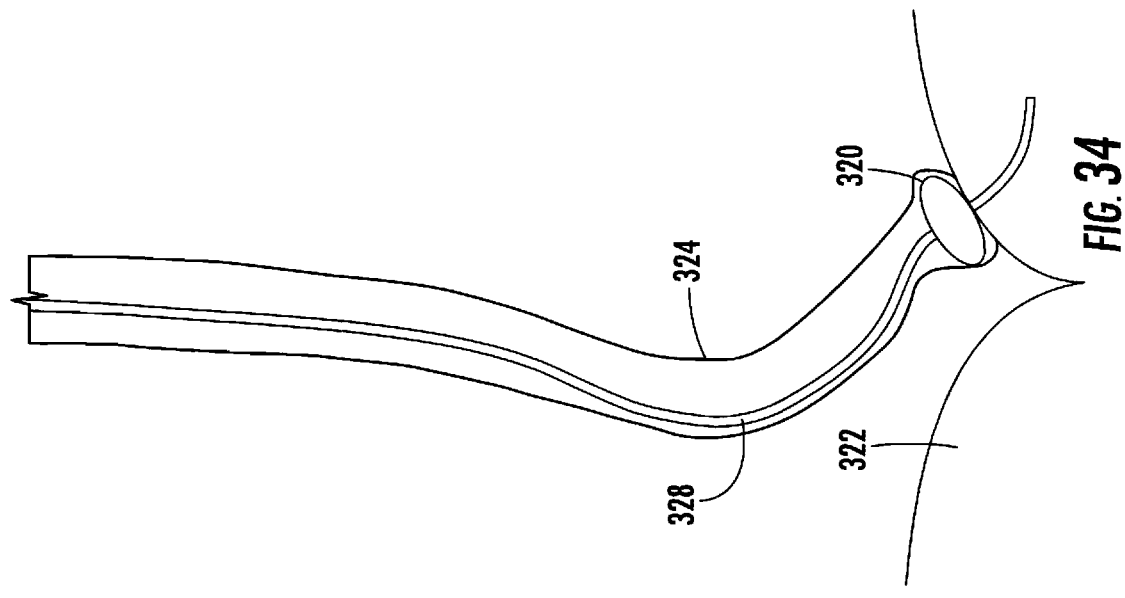
FIG. 34 is a schematic view illustrating the notched-body embodiment of FIG. 31 in a human anatomy.
Figure 33:
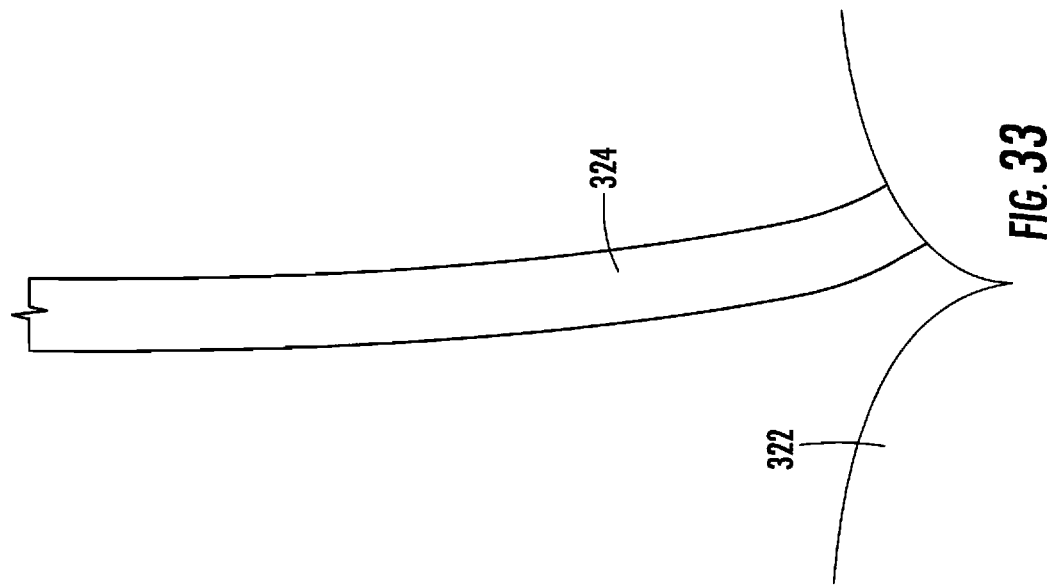
FIG. 33 is a schematic view of the esophagus and diaphragm to be displaced by the present invention.

An alternate embodiment of the gastric tube is disclosed in FIGS. 31-34. In this alternate embodiment of the gastric tube 300, the elongated flexible body 302 has various regions where the body is notched to allow curvature of the body 302. As shown in FIGS. 31-32, a construction allowing for a single curved operative section 304 is accomplished by three regions 308, 310 and 312 of notches 306. To provide an operative section 304 which deflects to the right, a first region 308 requires notches 306 on the left side of the flexible body 302, the second region 310 requires notches 306 on the right side of the flexible body 302, and the third region 312 requires notches 306 on the left side of the flexible body 302. As the flexible body experiences a compressive force, the flexible body 302 will curve towards the notches 306, creating a curve in the flexible body 302.

The compressive force can be accomplished in two ways. In FIG. 32, the flexible body 302 is shown with a control wire 314 positioned within a first lumen 316 within the flexible body 302. The control wire 314 is attached to the flexible body 302 on a distal end 318, so that pulling on the control wire 314 provides a compressive force on the flexible body 302. Alternatively, as shown in FIG. 31, a balloon 320 is included, which can be inflated near the flexible body's distal end 318. The balloon 320 is inflated through a cannula (not shown). When the balloon 320 is inflated, it creates a barrier preventing the gastric tube 300 from extending through the diaphragm 322. By exerting a force pushing the gastric tube 300 further into the esophagus 324, and the balloon 320 preventing the gastric tube 300 from passing the diaphragm 322, the gastric tube 300 experiences a compressive force, causing the three sections 308, 310, 312 to create a curve at the operative section 304 to deflect the esophagus 324. A membrane (not shown) can be included to prevent the notches 306 from pinching the esophagus 324.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An improved gastric tube for displacing a section of an esophagus during cardiac ablation procedures comprising:
    an elongated flexible tube constructed and arranged to be inserted in an esophagus of a patient and having a length to extend past an operative section of the patients anatomy, said operative section being the portion of the esophagus which overlies the heart,
    said elongated flexible tube having a first lumen constructed and arranged to extend the length of said elongated flexible tube, said elongated flexible tube having at least one control wire lumen having a proximal end constructed and arranged to receive at least one control wire for deflecting the esophagus away from the heart, and
    at least one secondary elongated flexible tube constructed and arranged to extend to at least said operative section, said at least one secondary elongated flexible tube having a lumen, said at least one secondary elongated flexible tube lumen having a proximal end, said proximal end connected to said elongated flexible tube, said at least one secondary elongated flexible tube lumen having a distal end, said distal end connected to said elongated flexible tube, a portion of said secondary elongated flexible tube proximate said operative section not connected to said elongated flexible tube, said at least one secondary elongated flexible tube including at least one aperture between said proximal end and said distal end, said at least one elongated flexible tube including a separation wire, said separation wire adapted to separate said secondary elongated flexible tube away from said elongated flexible tube in said operative section of said secondary elongated flexible tube,
    at least one temperature probe, said at least one temperature probe including at least one sensor for measuring temperature, said at least one sensor positioned within said at least one secondary elongated tube lumen along said operative section thereof,
    wherein said elongated tube is adapted to be positioned along a first wall of said esophagus to deflect said esophagus away from the heart of a patient in said operative section and wherein said secondary elongated flexible tube is positioned along a second wall of said esophagus towards the heart of a patient in said operative section when said at least one separation wire is operated from said proximal end of said secondary elongated flexible tube.

2. The improved gastric tube of claim 1, wherein said at least one secondary elongated tube lumen includes an inlet valve.

3. The improved gastric tube of claim 1, wherein said first lumen further comprises a secondary inlet, said secondary inlet including a valve.

4. The improved gastric tube of claim 1, wherein said at least one temperature probe comprising a wire with a proximal end and a distal end, said proximal end of said at least one temperature probe wire including a standard thermocouple connector, said distal end of said at least one temperature probe wire coupled to said secondary elongated tube lumen distal end.

5. The improved gastric tube of claim 4, wherein said temperature probe wire is a nitinol material wire, said nitinol wire operated by temperature to curve causing said separation between said elongated flexible tube and said secondary elongated flexible tube.

6. The improved gastric tube of claim 1, further comprising at least one 3D mapping wire, said at least one 3D mapping wire having a proximal end and a distal end, said proximal end of said at least one 3D mapping wire electrically coupled to an EP catheter 3D map connector, said at least one 3D mapping wire including a plurality of 3D mapping electrodes, said at least one 3D mapping wire positioned within said at least one secondary elongated tube lumen, said distal end of said at least one 3D mapping wire coupled to said distal end of said at least one secondary elongated tube lumen.

7. The improved gastric tube of claim 6, whereby said at least one control wire lumen is a pair of opposing control wire lumens, each of said opposing control wire lumens including an opposing control wire, said pair of opposing control wires having a distal end coupled to said distal end of said improved gastric tube, said pair of opposing control wires having a proximal end coupled to a tension control, whereby operation of tension control simultaneously increases tension in a first control wire while decreasing tension in a second control wire to result in deformation of said improved gastric tube.

8. The improved gastric tube of claim 7, further comprising a housing, said housing coupled to said proximal end of said elongated flexible body and said proximal end of said at least one secondary elongated flexible body, said housing coupled to said at least one secondary elongated flexible body lumen inlet valve, said housing coupled to said tension control, said housing coupled to said EP catheter 3D map connector, said housing coupled to a thermocouple connector.

9. The improved gastric tube of claim 8, further comprising a tension wire slide pull coupled to said housing, said tension wire slide pull in frictional contact with said pair of opposing control wires.

10. The improved gastric tube of claim 9, wherein said tension wire slide pull comprises an upper slide pull and a lower control wire guide, said upper slide pull frictionally connected to said lower control wire guide, said lower control wire guide directing said first and second control wires to opposing sides of said tension control.

11. The improved gastric tube of claim 10, wherein said tension control is a deflection disk.

* * * * *